(12) United States Patent
Zihlmann et al.

(10) Patent No.: US 10,960,107 B2
(45) Date of Patent: Mar. 30, 2021

(54) COLLAGEN MATRIX OR GRANULATE BLEND OF BONE SUBSTITUTE MATERIAL

(71) Applicant: GEISTLICH PHARMA AG, Wolhusen (CH)

(72) Inventors: Claudio Zihlmann, Lucerne (CH); Michael Bufler, Reinach (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 16/900,262

(22) Filed: Jun. 12, 2020

(65) Prior Publication Data
US 2020/0390934 A1    Dec. 17, 2020

(30) Foreign Application Priority Data

Jun. 14, 2019   (EP) .................................... 19180350

(51) Int. Cl.
| | | |
|---|---|---|
| A61L 27/24 | (2006.01) | |
| A61L 27/12 | (2006.01) | |
| A61L 27/38 | (2006.01) | |
| A61L 27/46 | (2006.01) | |
| A61L 2/08 | (2006.01) | |

(52) U.S. Cl.
CPC ............. *A61L 27/24* (2013.01); *A61L 27/12* (2013.01); *A61L 27/3847* (2013.01); *A61L 27/46* (2013.01); *A61L 2/082* (2013.01); *A61L 2202/11* (2013.01); *A61L 2202/21* (2013.01); *A61L 2400/12* (2013.01)

(58) Field of Classification Search
CPC ....... A61L 27/24; A61L 27/12; A61L 27/3847
See application file for complete search history.

(56) References Cited

U.S. PATENT DOCUMENTS

| | | |
|---|---|---|
| 5,167,961 A | 12/1992 | Heinz |
| 5,352,715 A | 10/1994 | Wallace et al. |
| 5,958,504 A | 9/1999 | Lee |
| 7,322,825 B2 | 1/2008 | Szymaitis |
| 8,734,524 B2 | 5/2014 | Bufler |
| 9,066,995 B2 | 6/2015 | Bufler |
| 10,646,615 B2 * | 5/2020 | Zihlmann ............. A61L 27/425 |
| 2003/0026770 A1 | 2/2003 | Szymaitis |
| 2007/0026030 A1 | 2/2007 | Gill |
| 2012/0107401 A1 | 5/2012 | McKay |
| 2012/0130506 A1 | 5/2012 | Bufler |
| 2014/0127392 A1 | 5/2014 | Berckmans, III |
| 2015/0024023 A1 | 1/2015 | Gibson |
| 2016/0106674 A1 | 4/2016 | Scalesciani |
| 2016/0144071 A1 | 5/2016 | Bufler |
| 2019/0184059 A1 | 6/2019 | Zihlmann |
| 2019/0209735 A1 | 7/2019 | Suppiger et al. |
| 2019/0209737 A1 | 7/2019 | Zihlmann et al. |
| 2020/0016293 A1 | 1/2020 | Zihlmann et al. |

FOREIGN PATENT DOCUMENTS

| | | | |
|---|---|---|---|
| EP | 0 270 254 A2 | 6/1988 | |
| EP | 2826495 A1 | 1/2015 | |
| EP | 2654816 B1 | 11/2015 | |
| WO | 2010/149296 A1 | 12/2010 | |
| WO | 2012084214 A1 | 6/2012 | |
| WO | WO-2015007393 A1 * | 1/2015 | ............. A61L 27/32 |

OTHER PUBLICATIONS

A C Lawson and J T Czernuszka. Collagen—calcium phosphate composites. Proc. Instn. Mech. Engrs., vol. 212 Part H, 1998, 413-425. (Year: 1998).*
Google Scholar search—collagen matrix bone replacement CAP HAP hydroxyapatite Aug. 9, 2020 (Year: 2020).*
Geistlich Bio-Oss et al: "Proven Clinical Efficiency Key to Success of Nascent European Bone Graft Substitutes Market", PR Newswire, Sep. 6, 2004 (Sep. 6, 2004), XP55566242, Retrieved from the Internet: URL:https://www.geistlich-na.com/fileadmin/contenVGeistlich_USA/Documents/PDFs/Product_Brochures/GPNA-BoneSubstituteBrochure_2018.pdf.
Daniele Cardaropoli et al: "Bio-Oss collagen and orthodontic movement for the treatment of infrabony defects in the esthetic zone", The International journal of periodontics & restorative dentistry, Dec. 1, 2006 (Dec. 1, 2006), p. 553, XP55566245, United States Retrieved from the Internet: URL:http://coimplante.odo.br/Biblioteca/J%20Peridontics%20Restorative%20DenVprd_26_6_Cardaropoli_4.pdf.
Adileh Shirmohammadi et al., "Comparative Study on the Efficacy of Anorganic Bovine Bone (Bio-Oss) and Nanocrystalline Hydroxyapatite (Ostim) in Maxillary Sinus Floor Augmentation", International Scholarly Research Notices, vol. 2014, Jan. 1, 2014 (Jan. 1, 2014), pp. 1-7, XP55566246, DOI: 10.1155/2014/967091.
Borum-Nicholas, L., et al: "Surface modification of hydroxyapatite. Part I. Dodecyl alcohol", Biomateri, Elsevier Science Publishers BV., Barking, GB, vol. 24, No. 21, 1(2003), pp. 3671-3679.
Sheikh et al. "Natural graft tissues and synthetic biomaterials for periodontal and alveolar bone reconstructive applications: a review," Biomaterials Research, published Jun. 5, 2017, p. 1-20.
Gittens et al. Implant Osseointegration and the Role of Microroughness and Nanostructures: Lessons for Spine Implants. Acta Biomater. Author manuscript. Aug. 1, 2015. (Year: 2015).
European Search Report cited in EP 19 18 0350 dated Dec. 3, 2019, 7 pages.

* cited by examiner

*Primary Examiner* — Michael P Cohen
(74) *Attorney, Agent, or Firm* — Rothwell, Figg, Ernst & Manbeck, P.C.

(57) ABSTRACT

A collagen matrix, granulate blend, and process for making and using a collagen matrix or granulate blend including collagen and particles or granules of a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets.

20 Claims, 7 Drawing Sheets

Fig. 4
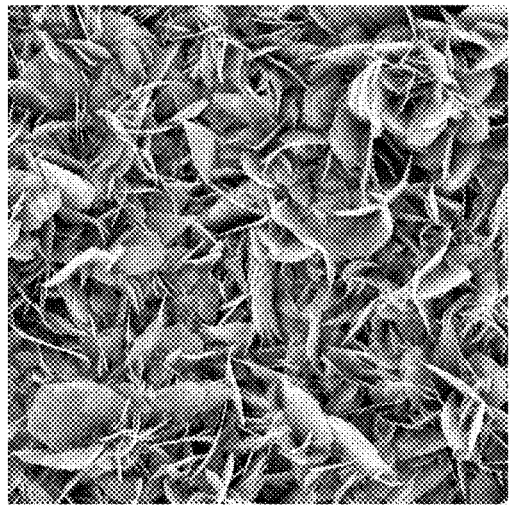
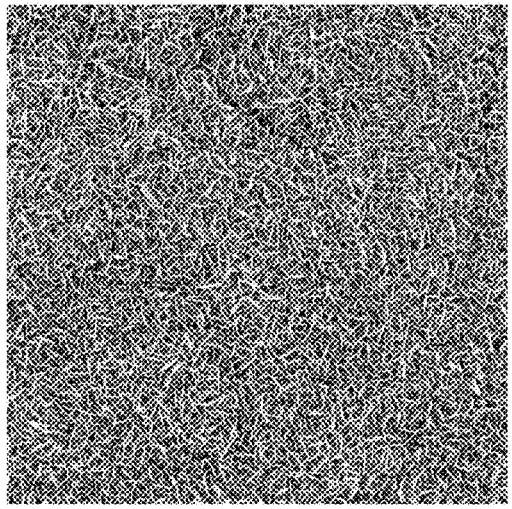
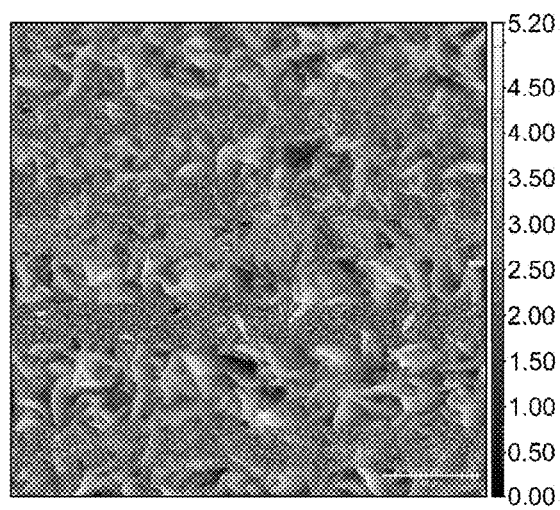
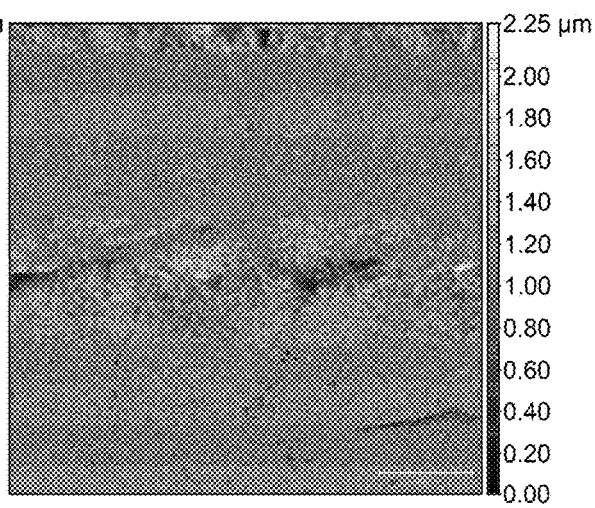
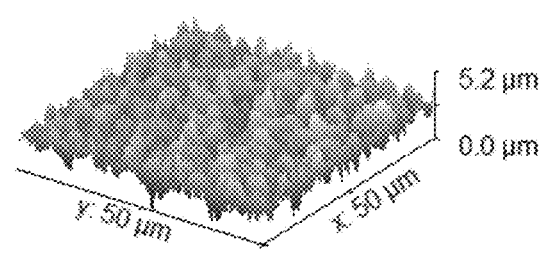
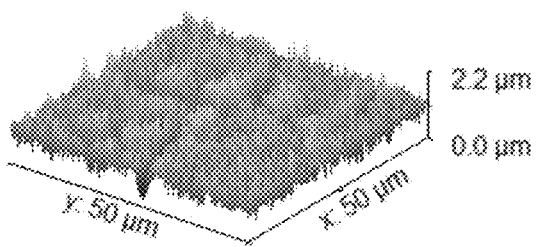

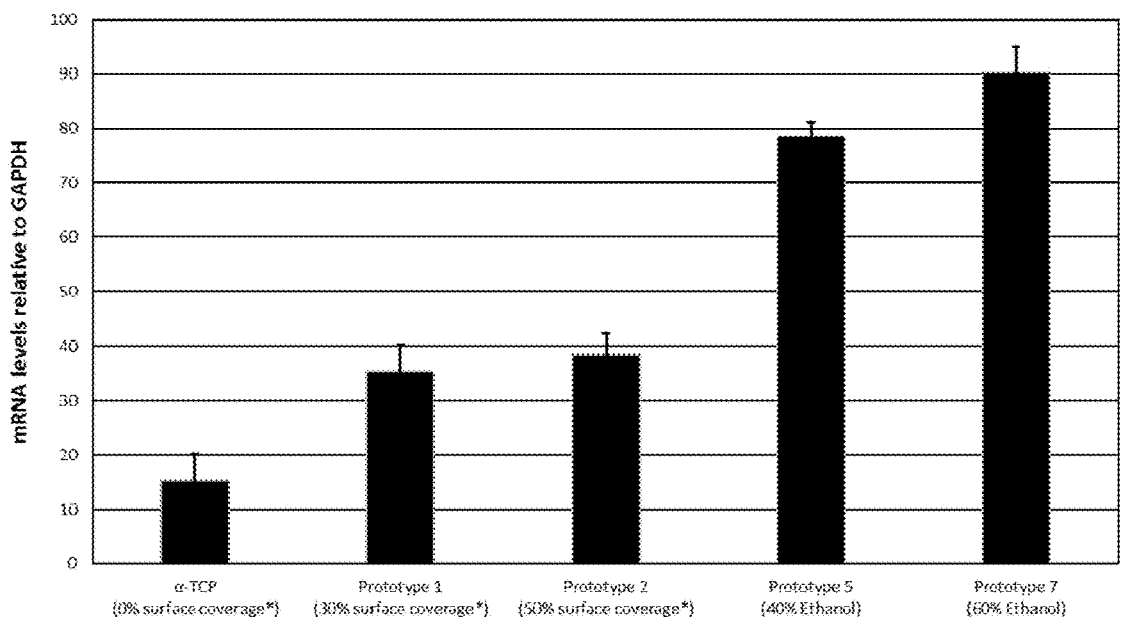
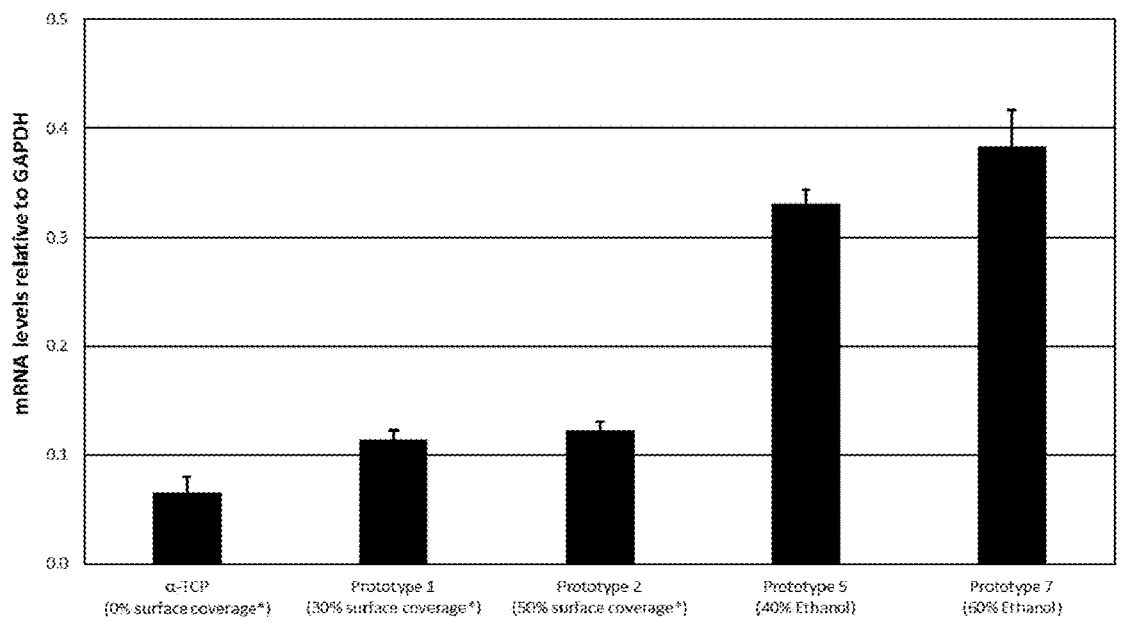
* surface coverage by individual clusters of flat crystal platelets as measured by SEM

COLLAGEN MATRIX OR GRANULATE BLEND OF BONE SUBSTITUTE MATERIAL

CROSS-REFERENCE TO RELATED APPLICATIONS

The present application claims priority benefit of European Patent Application No. 19180350.1, filed on Jun. 14, 2019, the disclosure of which is incorporated herein by reference.

BACKGROUND

The invention relates to a new collagen matrix, in particular for use as a putty, a strip or a plug—e.g. an oral plug—material, which comprises particles of a biphasic bone substitute material with a bilayer structure based on calcium phosphate/hydroxyapatite (CAP/HAP) which has an homogeneous external surface, a process for preparing that collagen matrix, as well as a new granulate blend comprising particles of such a biphasic bone material.

In the medical field, in particular in the field of orthopedics, a putty is generally defined as a compound with a playdough-like consistency with suitable moldability and cohesiveness characteristics. A putty material can be readily manually shaped and retains its shape once the external force is removed.

A strip is generally defined as a flexible and form-stable material which can fit the anatomic curvature of the graft site. A strip can be compressed and folded but goes back to its original shape once the external force is removed.

A plug is generally defined as a cylindrical- or cone-shaped material with different dimensions. The material is flexible and can be compressed but goes back to its original shape once the external force is removed. An oral plug is a plug that can be used in the oral cavity. It can in particular be used to fill a hole or a cavity such as a socket after tooth extraction.

Defects in bone structure arise in a variety of circumstances, such as trauma, disease, and surgery and there is still a need for effective repair of bone defects in various surgical fields.

Numerous natural and synthetic materials and compositions have been used to stimulate healing at the site of a bone defect. A well-known natural, osteoconductive bone substitute material that promotes bone growth in periodontal and maxillofacial osseous defects is Geistlich Bio-Oss®: commercially available from Geistlich Pharma AG. That material is manufactured from natural bone by a process described in U.S. Pat. No. 5,167,961, which enables preservation of the trabecular architecture and nanocrystalline structure of the natural bone, resulting in an excellent osteoconductive matrix which is not or very slowly resorbed.

Tricalcium phosphate/hydroxyapatite (TCP/HAP) systems and their use as bone substitute materials are described, for example, in U.S. Pat. No. 6,338,752 disclosing a process for preparing a biphasic cement of α-TCP/HAP by heating a powder mixture of ammonium phosphate and HAP at 1200-1500° C.

European Patent EP-285826 describes a process for the production of a layer of HAP on metallic and non-metallic bodies for implants by application of a layer of α-TCP and completely converting the α-TCP layer into HAP by reaction with water of pH 2 to 7 at 80-100° C. The product obtained is a metallic or non-metallic body covered with a layer of HAP.

WO 97/41273 describes a process for coating a substrate such as notably hydroxyapatite (HAP) or other calcium phosphates (CAP) with a coating of carbonated hydroxyapatite, i.e. hydroxyapatite wherein phosphate and/or hydroxyl ions are partially replaced by bicarbonate ions, by a process comprising (a) immersing the substrate in a solution of pH 6.8 to 8.0 containing calcium ions, phosphate ions and bicarbonate ions at a temperature lower than 50° C., (b) heating the portion of the solution in contact with the substrate to a temperature of 50 to 80° C. until having a pH greater than 8, (c) maintaining the substrate in contact with the alkali solution obtained in step (b) to form a carbonated hydroxyapatite coating, and (d) taking the substrate off the solution and subjecting the coating to drying. The bicarbonate ions are disclosed to act as inhibitors of hydroxyapatite crystal growth, resulting in non-stoichiometric crystals containing defects and having rather small dimensions, namely 10-40 nm in length and 3-10 nm in width (see page 7, lines 1-7).

The components of calcium phosphate/hydroxyapatite (CAP/HAP) systems, especially TCP/HAP systems differ in their thermodynamic stability. Due to this difference, when CAP/HAP systems are implanted into a mammal, in particular a human patient, the solubility of TCP and other calcium phosphates is higher in the body fluid than the solubility of HAP. The difference in solubility between calcium phosphates and HAP causes a breakdown of the unordered sinter structure of the CAP/HAP system because the better soluble compound CAP (e.g. TCP) is removed quicker than HAP. The sintered interconnection between CAP and HAP produced at high temperatures will also make a remarkable contribution to higher solubility of the device in the physiological environment. Two different types of reactions dominate accelerated in vivo degradation of such ceramics: chemical dissolution and biological resorption by cells. Both processes cause dissolution of the ceramic material which furthermore causes a local oversaturation of calcium ions, whereby there are more calcium ions released than calcium ions adsorbed. The natural equilibrium of calcium ions no longer exists, neither in the extracellular matrix nor in the tissue surrounding of the implant. The local disturbance of the natural calcium equilibrium in terms of oversaturation of calcium ions leads to an increased osteoclast activity and therefore to an accelerated ill-controlled resorption of the ceramic material and a risk of adverse inflammation reactions, especially when using a large amount of synthetic bone substitute material.

When bone substitute material Geistlich Bio-Oss® is implanted into a human patient, the natural calcium equilibrium is practically not affected, the concentration of calcium ions on the surface of the material and within the local environment thereof remaining almost constant. Biological resorption of the material hence does not take place or proceeds at a very slow rate without the risk of adverse inflammation reactions.

EP-B1-2445543 discloses a highly advantageous calcium phosphate/hydroxyapatite (CAP/HAP) bone substitute material which, like bone substitute material Geistlich Bio-Oss®, after being set in vivo enables the concentration of calcium ions on the surface of the material and within the local environment thereof to remain almost constant and thus does not lead to an increased osteoclast activity.

Indeed, the natural calcium equilibrium which is necessary for optimal bone regeneration is not disturbed or destroyed. Moreover, the natural calcium concentration equilibrium is lastingly supported by the bone substitute material until the regeneration process is completed. When those conditions are met there is no increase of osteoclast activity, hence no risk of adverse inflammation reactions.

The invention of EP-B1-2445543 relates to a biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm.

The sintered CAP core may comprise tricalcium phosphate (TCP), notably α-TCP (α-Ca$_3$(PO$_4$)$_2$) or β-TCP (β-Ca$_3$(PO$_4$)$_2$), and/or tetracalcium phosphate (TTCP) Ca$_4$(PO$_4$)$_2$O.

According to a frequently used embodiment the sintered CAP core essentially consists of TCP, α-TCP being preferred. As used herein, the phrase "essentially consists of" means that the material includes TCP and materials that do not materially affect the basic and novel characteristics of the claimed invention.

The epitactically grown layer of nanocrystalline HAP is structurally and chemically nearly identical to the natural human bone mineral.

The epitactically grown layer of nanocrystalline HAP generally has a thickness of at least from 15 to 50 nm, preferably at least from 20 to 40 nm, more preferably at least from 25 to 35 nm. That minimum thickness corresponds to one layer of HAP nanocrystals in epitaxial orientation.

The epitactically grown layer of nanocrystalline HAP may comprise a single or multiple layers of HAP nanocrystals in epitaxial orientation. The thickness of the epitactically grown layer of nanocrystalline HAP, which is related to the number of such layers of HAP nanocrystals in epitaxial orientation, will be selected according to the intended application of the bone substitute material as implant or prosthesis in differently loaded parts of the body. The bone substitute material of that invention is indeed designed to function in vivo as a living-like system progressively transforming the sintered CAP core into hydroxyapatite similar in size and morphology to human bone mineral, the rate of that transformation being dependent on the rate of calcium release by the sintered CAP core, which is to a large extent controlled by the thickness of the epitactically grown layer of nanocrystalline HAP.

The properties of the CAP/HAP bone substitute material are to a large extent controlled by the thickness of the epitactically grown layer of crystalline HAP. The term "properties" includes the ability of the CAP/HAP bone substitute to release a constant concentration of calcium ions to the local environment in vitro and in vivo.

The thickness of the epitactically grown layer of nanocrystalline HAP is related to the ratio of the sintered CAP core material to HAP, said ratio being generally between 5:95 and 95:5, preferably from 10:90 to 90:10.

The CAP/HAP bone substitute material may be a particulate or a granulate, the particles or granules having a desired size and shape. Generally, the particles or granules are approximately spherical and have a diameter of 250 to 5000 μm.

The CAP/HAP bone substitute material may also be a shaped body, e.g. a screw, a nail, a pin or a structure having the profile of an osseous body part such as notably a hip, a clavicle, a rib, a mandible or a skull part. Such a screw, a nail or a pin may be used in reconstructive orthopedic surgery for fixing a ligament to a bone, for example in the knee or the elbow. Such a structure having the profile of an osseous body part may be used in orthopedic surgery as prosthesis for replacing a missing or defective bone or bone part.

That CAP/HAP bone substitute material of EP-B1-2445543 is taught to be obtained by a process comprising the steps of
  a) preparing a sintered CAP core material,
  b) immersing the sintered CAP core material in an aqueous solution at a temperature between 10° C. and 50° C. to start the transformation process of CAP to HAP, whereby a uniform and closed epitactically grown layer of nanocrystalline hydroxyapatite is formed on the sintered CAP core material surface, the epitactically grown nanocrystals having the same size and morphology as human bone mineral,
  c) stopping the transformation by separating the solid material from the aqueous solution at a time when a uniform and closed coating of at least one nanocrystalline layer of HAP is present but before the transformation process is finished completely,
  d) optionally sterilizing the separated material coming from step c).

The preparation of the sintered CAP core material may be performed by methods known in the art comprising first mixing powders of calcium hydrogen phosphate (CaHPO$_4$), calcium carbonate and/or calcium hydroxide, then calcining and sintering the mixture within an appropriate temperature range, thereby giving a bulk sintered CAP core material (see e.g. Mathew M. et al., 1977, Acta. Cryst. B33: 1325; Dickens B. et al., 1974, J. Solid State Chemistry 10, 232; and Durucan C. et al., 2002, J. Mat. Sci., 37:963).

A bulk sintered TCP core material may thus be obtained by mixing powders of calcium hydrogen phosphate (CaHPO$_4$), calcium carbonate and/or calcium hydroxide in stoichiometric ratio, calcining and sintering the mixture at a temperature in the range of 1200-1450° C., preferably about 1400° C.

A bulk sintered TTCP core material may also be obtained by the above described process.

The bulk sintered CAP material prepared by such methods may be porous with a porosity of 2 to 80 vol % and a wide distribution of pores. The porosity parameters will be selected according to the intended application of the CAP/HAP bone substitute material.

The sintered CAP core material used in step b) may be
  the bulk sintered CAP core material prepared as described above,
  a particulate or granulate of sintered CAP core material obtained from the bulk sintered CAP core material prepared as described above, by using conventional methods such as crushing, grinding and/or milling, and sieving, or
  a preform of sintered CAP core material having a desired shape and size, e.g. a screw, a nail, a pin or a structure having the profile of an osseous body part.

Such a preform of any desired shape and size may be obtained from the bulk sintered core material prepared as described above, by using well known prototyping techniques such as CNC milling or 3D printing (see for example Bartolo P. et al., 2008, Bio-Materials and Prototyping Applications in Medicine, Springer Science New York, ISBN 978-0-387-47682-7; Landers R. et al., 2002, Biomaterials 23(23), 4437; Yeong W.-Y. et al., 2004, Trends in Biotechnology, 22 (12), 643; and Seitz H. et al., 2005, Biomed. Mater. Res. 74B (2), 782).

The aqueous solution of step b) is taught to be pure water, a simulated body fluid or a buffer. Important is that the pH value of the immersing solution of step b) is nearly neutral and remains stable throughout the transformation process, preferably within a pH range from 5.5 to 9.0.

The term "simulated body fluid" refers to any solution that mimics a body fluid. Preferably, the simulated body fluid has an ion concentration similar to that of blood plasma.

The buffer may be any buffer in the above pH range but is preferably a phosphate buffer with or without calcium, magnesium and/or sodium.

The buffer used in the Examples (see Examples 4 and 5) is an aqueous phosphate buffer.

The temperature range in step b) is generally between 10° C. and 50° C., preferably between 25 and 45° C., more preferably between 35° C. and 40° C.

The immersing step b) induces in a first phase a first-order phase transition of the CAP core material and therefore the nucleation of HAP nanocrystal precursors. During the second phase the resulting HAP precursors from the first phase will grow and establish a closed (i.e. completely coating) epitactic nanocrystalline composite layer. The first HAP nanocrystal layer must be uniform and closed and epitaxially connected to the sintered CAP core material.

During a third phase the first-order phase transition may proceed within the newly formed bilayer composite to further transform the sintered CAP core material (TCP or TTCP) into nanocrystalline HAP. During this third step of phase transition calcium ions will be released for a controllable time by a slow diffusion controlled process until a part of the sintered CAP core material has been transformed into nanocrystalline HAP. The thickness of the HAP layer and therefore the rate of calcium release can be controlled by variation of the transformation time.

The epitactically grown nanocrystalline HAP layer of appropriate thickness will be prepared in vitro, the transformation of CAP into HAP being stopped before it is completed.

As soon as the CAP/HAP bone substitute material is set in vivo, the transformation process of CAP into HAP will be reactivated by contact with the body fluids and the bone substitute material will function as a living-like system forming new hydroxyapatite similar in size and morphology to human bone mineral. During the in vivo phase transformation process the transported calcium ions will be released into the local environment supporting the local calcium equilibrium which is important and beneficial for bone regeneration processes.

Due to different regeneration times of bone defects in differently loaded regions of the body it is important that the rate of calcium release can be controlled. This can be achieved by variation of the thickness of the epitactically grown layer of hydroxyapatite.

Step c) is therefore a very critical step. The exposure time in the aqueous solution of step b) is based upon the thickness of the HAP layer desired. At least one layer of nanocrystalline HAP in epitaxial orientation is necessary. It is essential that the transformation of CAP into HAP is not finished.

The proper exposure time according to the thickness desired can be calculated by using several thermodynamic differential equations well known to the skilled person in the art of calcium phosphates, cement and concrete chemistry. See for example: Pommersheim, J. C.; Clifton, J. R. (1979) Cem. Conc. Res.; 9:765; Pommersheim, J. C.; Clifton, J. R. (1982) Cem. Conc. Res.; 12:765; and Schliissler, K. H. Mcedlov-Petrosjan, O. P.; (1990): Der Baustoff Beton, VEB Verlag Bauwesen, Berlin.

Transferring the solution of the above mentioned differential equations to the CAP/HAP system enables the prediction of the phase transition of CAP into HAP and the thickness of the layer such that the epitactic layer of HAP can be prepared in a stable and reproducible manner.

Separating the solid material from the aqueous solution at the end of step c) is usually performed by filtration, washing and drying, using techniques well known in the art.

In the Examples of EP-B1-2445543 (namely Example 4 [0057] and Example 5 [0058]), washing is performed by washing the separated granules of the bone substitute 3 times with purified water to remove residuals from the buffered solution.

The optional sterilizing step d) may be performed by techniques well known in the art such as gamma-irradiation or X-ray radiation.

Using as taught in Examples 4 and 5 of EP-B1-2445543 an aqueous phosphate buffer for the aqueous solution of step b) and purified water to wash 3 times the separated granules at the end of step c), one obtains a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a non-homogeneous external surface comprising individual (separated) clusters of flat crystal platelets consisting of epitactically grown HAP nanocrystals and smooth areas between the individual clusters of flat crystal platelets, the % of the external surface occupied by the smooth areas between the individual clusters of flat crystal platelets depending on the transformation time in given transformation conditions.

See FIG. 1A, which represents a SEM (scanning electron microscopy) picture of prototype 1 (1-2 mm granule) having a transformation time of 30 min wherein the smooth areas represent about 70% of the total external surface as measured by SEM and FIG. 1B, which represents an SEM picture of prototype 2 (1-2 mm granule) having a transformation time of 40 min wherein the smooth areas represent about 50% of the total external surface as measured by SEM.

WO 2015/009154 discloses a method for producing an osteoconductive material with improved osteoinductive capacity, which comprises subjecting a sintered biphasic calcium phosphate/hydroxyapatite (CAP/HAP) material having a surface topography consisting of grains to a hydrothermal treatment under a pressure of 2-4 bars at a temperature equal to or higher than 125° C. without controlling the pH for a duration sufficient to change calcium phosphate grains on the surface of the starting material into calcium phosphate needles of a diameter 10-1500 nm. A temperature of at least 125° C. and a pressure of at least 2 bars is far from the (close to the human body physiological) conditions used in EP-B1-2445543 (temperature 35-40° C., pH 5.5-9.0, ambient pressure) which enable epitactic growth of HAP nanocrystals. Those needles are not epitactically grown but attached to or deposited on the core material and only partially (usually 40-90%) coat the latter, thereby increasing its specific surface and capacity of harboring proteins, thus enhancing its osteoinductive potential.

The inventors of international PCT patent application WO-2019/115704 found that by adding 10 to 90%, preferably 20 to 60%, of a short-chain aliphatic alcohol including but not limited to methanol, ethanol, propanol or butanol to the aqueous phosphate buffer of step b) in preparation of the biphasic calcium phosphate/hydroxyapatite (CAP/HAP)

bone substitute material according to EP-B1-2445543, the non-homogeneous external surface of the closed epitactically grown layer of nanocrystalline HAP deposited on the external surface of the sintered CAP core biphasic calcium phosphate/hydroxyapatite (CAP/HAP) bone substitute material, which comprises individual clusters of flat crystal platelets and smooth areas in between, is replaced by a homogeneous coarse external surface comprising flat crystal platelets without any individual crystal clusters of flat crystal platelets. That homogeneous coarse external surface generally comprises epitactically grown nanocrystalline hydroxyapatite platelets forming an interlocked network of platelets with individual platelet sizes of 0.2 to 20 µm, preferably 0.5 to 5 µm, as determined by SEM, depending on the amount of aliphatic alcohol used.

As shown by in vitro tests of osteogenic differentiation of fetal human mesenchymal stem cells (hMSCs), the in vivo osteogenic response is likely to be stronger for the biphasic calcium phosphate/hydroxyapatite (CAP/HAP) bone substitute material having that homogeneous coarse external surface comprising flat crystal platelets than for the biphasic calcium phosphate/hydroxyapatite (CAP/HAP) bone substitute material taught by EP-B1-2445543 which has a non-homogeneous external surface comprising individual clusters of flat crystal platelets and smooth areas in between.

The invention of international PCT patent application WO-2019/115704 thus concerns a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets.

That biphasic calcium phosphate/hydroxyapatite (CAP/HAP) bone substitute material shows an increased osteogenic differentiation of fetal human mesenchymal stem cells (hMSCs), which is a strong indication of an enhanced in vivo osteogenic response.

The term "closed epitactically grown layer of nanocrystalline HAP deposited on the external surface of the sintered CAP core" means that the epitactically grown layer of nanocrystalline HAP completely covers the entire external surface of the sintered CAP core.

The term "homogeneous coarse external surface comprising flat crystal platelets" means that macroscopically the coarseness of the external surface caused by the flat crystal platelets is statistically evenly distributed on the surface of the CAP core without individual crystal clusters of flat crystal platelets. See FIGS. 2A-2E which represent SEM pictures of prototypes 3 to 7 of the biphasic calcium phosphate/hydroxyapatite (CAP/HAP) bone substitute material of the invention with a homogeneous coarse external surface with a varying degree of coarseness.

The term "flat crystal platelets" means crystal assemblies where the height (thickness) is considerably smaller than the width and length with respect to the three perpendicular directions. Such flat crystal platelets are clearly visible in FIG. 3B.

Generally, the homogeneous coarse external surface comprises epitactically grown nanocrystalline hydroxyapatite platelets forming an interlocked network of platelets with sizes (width and length) of 0.2 to 20 µm as determined by SEM. The larger the sizes of the platelets, the higher the coarseness of the external surface.

Preferably, the homogeneous coarse external surface comprises epitactically grown nanocrystalline hydroxyapatite platelets forming an interlocked network of platelets with sizes of 0.5 to 5 µm as determined by SEM Usually, that homogeneous coarse external surface comprises epitactically grown hydroxyapatite platelets forming an interlocked network containing pores between 0.03 and 2 µm as determined by Mercury Intrusion Porosimetry (MIP). The higher the pore volume between 0.03 and 2 µm is, the higher is the coarseness of the external surface.

Generally, that homogeneous coarse external surface may be characterized by AFM (Atomic Force Microscopy) with an AFM-derived root mean square roughness ($R_q$) in a range of 50 to 400 nm and an average maximum height of the profile ($R_z$) in a range of 500 to 2000 nm.

Preferably, the homogeneous coarse external surface may be characterized by an AFM-derived root mean square roughness ($R_q$) in a range of 110 to 150 nm and an average maximum height of the profile ($R_z$) in a range of 550 to 750 nm.

Generally, the percentage of HAP in the biphasic calcium phosphate/hydroxyapatite (CAP/HAP) bone substitute material is from 1 to 90%, as measured by XRD.

Preferably, that percentage is from 1.5 to 30%, more preferably from 2 to 15%, as measured by XRD.

The sintered CAP core comprises tricalcium phosphate (TCP), notably α-TCP (α-$Ca_3(PO_4)_2$) or β-TCP (β-$Ca_3(PO_4)_2$), and/or tetracalcium phosphate (TTCP) $Ca_4(PO_4)_2$ O.

According to a frequently used embodiment the sintered CAP core essentially consists of TCP, α-TCP being preferred.

The epitactically grown layer of nanocrystalline HAP is structurally nearly identical to the natural human bone mineral.

The CAP/HAP bone substitute material may be a particulate or a granulate, the particles or granules having a desired size and shape. Generally, the particles or granules have a size of 250 to 5000 µm, preferably 1000 to 2000 µm.

The CAP/HAP bone substitute material may also be a shaped body, e.g. a screw, a nail, a pin or a structure having the profile of an osseous body part such as notably a hip, a clavicle, a rib, a mandible or a skull part. Such a screw, a nail or a pin may be used in reconstructive orthopedic surgery for fixing a ligament to a bone, for example in the knee or the elbow. Such a structure having the profile of an osseous body part may be used in orthopedic surgery as prosthesis for replacing a missing or defective bone or bone part.

The invention of international PCT patent application WO-2019/115704 also relates to a putty comprising particles or granules of the above defined CAP/HAP bone substitute in a suitable matrix, generally comprising natural or synthetic polymers. Generally, the particles or granules have a size of 250 to 5000 µm, preferably 1000 to 2000 µm.

The invention of international PCT patent application WO-2019/115704 further relates to a process of preparing the above defined CAP/HAP bone substitute material comprising the steps of
a) preparing a sintered CAP core material,
b) immersing the sintered CAP core material in a buffer solution containing 10 to 90% of a short-chain aliphatic alcohol at a temperature between 10° C. and 50° C. to start the transformation process of CAP to HAP whereby a closed epitactic grown layer of nanocrystalline hydroxyapatite will be formed on the sintered CAP core material surface, whereby the epitactically grown nanocrystals have the same size and morphology as human bone mineral, wherein the closed epitactically grown layer of nanocrystalline HAP formed on the sintered CAP core material surface has a homogeneous external surface comprising flat crystal platelets, c) stopping the transformation by separating solid material from the aqueous solution at a time when a closed coating of at least one nanocrystalline layer of HAP is present but before the transformation process is finished completely, and d) optionally sterilizing the separated material coming from step c).

A suitable short-chain aliphatic alcohol may be selected from the group consisting of methanol, ethanol, propanol and butanol.

Preferably the short-chain aliphatic alcohol is ethanol.

Preferably, the buffer solution of step b) contains 20 to 60%, more preferably 30 to 50%, of a short-chain aliphatic alcohol.

The coarseness parameters of the homogeneous coarse external surface of the closed epitactically grown layer of nanocrystalline HAP deposited on the external surface of the sintered CAP core, notably the AFM parameters: the AFM-derived root mean square roughness ($R_q$) and the average maximum height of the profile ($R_z$), the sizes of the epitactically grown nanocrystalline hydroxyapatite platelets as determined by SEM and the volume of pores between 0.03 and 2 µm as determined by MIP can conveniently be adjusted by changing the percentage of the short-chain aliphatic alcohol in the buffer solution of the transformation solution.

The higher that percentage is, the lower are the AFM-derived root mean square roughness ($R_q$) and the average maximum height of the profile ($R_z$), the smaller are the sizes of the epitactically grown nanocrystalline hydroxyapatite platelets as determined by SEM and the smaller is the volume of pores between 0.03 and 2 µm as determined by MIP.

The buffer solution of step b) containing 10 to 90% of a short-chain aliphatic alcohol is obtained by mixing an aqueous buffer solution with varying amounts of a short-chain aliphatic alcohol. The aqueous buffer solution is chosen such that the pH value of the immersing solution of step b) which further contains 10 to 90% of a short-chain aliphatic alcohol is nearly neutral and remains stable throughout the transformation process, preferably within a pH range from 5.5 to 9.0, more preferably from 7.0 to 8.0.

The buffer may be any buffer in the above pH range but is preferably a phosphate buffer with or without calcium, magnesium and/or sodium.

A suitable buffer solution is e.g. a 0.05-0.3 M aqueous solution of sodium dihydrogen phosphate ($NaH_2PO_4$) with a pH value of 7.3 to 7.6.

The temperature range in step b) is generally between 10° C. and 50° C., preferably between 25 and 45° C., more preferably between 35° C. and 40° C.

Preferably step b) is carried out at a temperature of 35 to 40° C. in a phosphate buffer solution of pH from 7.0 to 8.0 containing 20 to 60% of a short-chain aliphatic alcohol.

The preparation of the sintered CAP core material may be performed by methods known in the art comprising first mixing powders of calcium hydrogen phosphate ($CaHPO_4$), calcium carbonate and/or calcium hydroxide, then calcining and sintering the mixture within an appropriate temperature range, thereby giving a bulk sintered CAP core material (see e.g. Mathew M. et al., 1977, Acta. Cryst. B33: 1325; Dickens B. et al., 1974, J. Solid State Chemistry 10, 232; and Durucan C. et al., 2002, J. Mat. Sci., 37:963).

A bulk sintered TCP core material may thus be obtained by mixing powders of calcium hydrogen phosphate ($CaHPO_4$), calcium carbonate and/or calcium hydroxide in stoichiometric ratio, calcining and sintering the mixture at a temperature in the range of 1200-1450° C., preferably about 1400° C.

A bulk sintered TTCP core material may also be obtained by the above described process.

The bulk sintered CAP material prepared by such methods may be porous with a porosity of 2 to 80 vol % and a wide distribution of pores. The porosity parameters will be selected according to the intended application of the CAP/HAP bone substitute material.

The sintered CAP core material used in step b) may be
the bulk sintered CAP core material prepared as described above, a particulate or granulate of sintered CAP core material obtained from the bulk sintered CAP core material prepared as described above, by using conventional methods such as crushing, grinding and/or milling, and sieving, or a preform of sintered CAP core material having a desired shape and size, e.g. a screw, a nail, a pin or a structure having the profile of an osseous body part.

Such a preform of any desired shape and size may be obtained from the bulk sintered core material prepared as described above, by using well known prototyping techniques such as CNC milling or 3D printing (see for example Bartolo P. et al., 2008, Bio-Materials and Prototyping Applications in Medicine, Springer Science New York, ISBN 978-0-387-47682-7; Landers R. et al., 2002, Biomaterials 23(23), 4437; Yeong W.-Y. et al., 2004, Trends in Biotechnology, 22 (12), 643; and Seitz H. et al., 2005, Biomed. Mater. Res. 74B (2), 782).

The immersing step b) induces in a first phase a first-order phase transition of the CAP core material and therefore the nucleation of HAP nanocrystal precursors. During the second phase the resulting HAP precursors from the first phase will grow and establish a closed (i.e. completely coating) epitactic nanocrystalline composite layer. The first HAP nanocrystal layer must be uniform and closed and epitactically connected to the sintered CAP core material.

During a third phase the first-order phase transition may proceed within the newly formed bilayer composite to further transform the sintered CAP core material (TCP or TTCP) into nanocrystalline HAP. During this third step of phase transition calcium ions will be released for a controllable time by a slow diffusion controlled process until a part of the sintered CAP core material has been transformed into nanocrystalline HAP. The thickness of the HAP layer and therefore the rate of calcium release can be controlled by variation of the transformation time.

The epitactically grown nanocrystalline HAP layer of appropriate thickness will be prepared in vitro, the transformation of CAP into HAP being stopped before it is completed.

As soon as the CAP/HAP bone substitute material is set in vivo the transformation process of CAP into HAP will be reactivated by contact with the body fluids and the bone substitute material will function as a living-like system forming new hydroxyapatite similar in size and morphology to human bone mineral. During the in vivo phase transformation process the transported calcium ions will be released into the local environment supporting the local calcium equilibrium which is important and beneficial for bone regeneration processes.

Due to different regeneration times of bone defects in differently loaded regions of the body it is important that the rate of calcium release can be controlled. This can be achieved by variation of the thickness of the epitactically grown layer of hydroxyapatite.

Step c) is therefore a very critical step. The exposure time in the aqueous solution of step b) is based upon the thickness of the HAP layer desired. At least one layer of nanocrystalline HAP in epitaxial orientation is necessary. It is essential that the transformation of CAP into HAP is not finished.

The proper exposure time according to the thickness desired can be calculated by using several thermodynamic differential equations well known to the skilled person in the art of calcium phosphates and cement and concrete chemistry.

See for example: Pommersheim, J. C.; Clifton, J. R. (1979) Cem. Conc. Res.; 9:765; Pommersheim, J. C.; Clifton, J. R. (1982) Cem. Conc. Res.; 12:765; and Schlüssler, K. H. Mcedlov-Petrosjan, O. P.; (1990): Der Baustoff Beton, VEB Verlag Bauwesen, Berlin.

Transferring the solution of the above mentioned differential equations to the CAP/HAP system enables the prediction of the phase transition of CAP into HAP and the thickness of the layer such that the epitactic layer of HAP can be prepared in a stable and reproducible manner.

Separating the solid material from the aqueous solution is usually performed by filtration and drying, using techniques well known in the art.

The optional sterilizing step d) may be performed by techniques well known in the art such as gamma-irradiation or X-ray radiation.

Advantages of the CAP/HAP Bone Substitute Material of the Invention of International PCT Patent Application WO-2019/115704 and the Process of Preparation Thereof.

That biphasic calcium phosphate/hydroxyapatite (CAP/HAP) bone substitute material of the invention with a homogeneous coarse external surface comprising flat crystal platelets shows an increased osteogenic differentiation of fetal human mesenchymal stem cells (hMSCs), in particular a higher expression of differentiation markers osteopontin (OPN) and osteocalcin (OCN), compared with the biphasic calcium phosphate/hydroxyapatite (CAP/HAP) bone substitute material taught by EP-B1-2445543 which has a non-homogeneous external surface comprising individual clusters of flat crystal platelets and smooth areas in between. This is a strong indication of an enhanced in vivo osteogenic response.

This is in line with the results published by R. A. Gittens et al. in Biomaterials 2011 May, 32(13): 3395-3403, which show that the introduction of nanoscale structures in combination with micro-submicro-scale roughness improves osteoblast differentiation and local factor production, which in turn indicates the potential for improved implant osseointegration in vivo.

The process of preparation of the biphasic calcium phosphate/hydroxyapatite (CAP/HAP) bone substitute material of the invention allows to conveniently adjust the coarseness parameters of the homogeneous coarse external surface of the closed epitactically grown layer of nanocrystalline HAP deposited on the external surface of the sintered CAP core, notably the AFM parameters: AFM-derived root mean square roughness ($R_q$) and average maximum height of the profile ($R_z$), the sizes of the epitactically grown nanocrystalline hydroxyapatite platelets as determined by SEM and the volume of pores between 0.03 and 2 µm as determined by MIP, by adjusting the percentage of the short-chain aliphatic alcohol in the buffer solution of the transformation solution.

The higher that percentage is, the lower are the AFM-derived root mean square roughness ($R_q$) and the average maximum height of the profile ($R_z$), the smaller are the sizes of the epitactically grown nanocrystalline hydroxyapatite platelets as determined by SEM and the smaller is the volume of pores between 0.03 and 2 µm as determined by MIP.

SUMMARY OF THE INVENTION

As set forth above, international PCT patent application WO-2019/115704 discloses a putty material comprising particles or granules of the above defined CAP/HAP bone substitute in a suitable matrix, generally comprising natural or synthetic polymers. Generally, the particles or granules have a size of 250 to 5000 µm, preferably 1000 to 2000 µm. No specific synthetic or natural polymer is taught for the putty matrix.

That international application does not mention any strip, any plug or any granulate blend of that CAP/HAP bone substitute The applicant has now found how to prepare a putty with suitable handling properties comprising particles or granules of the above defined CAP/HAP bone substitute material in a collagen matrix and has tested such a putty in a rabbit posterolateral spinal fusion (PLF) model.

The applicant has also found how to prepare a strip and a plug of that CAP/HAP bone substitute material in a collagen matrix and a new granulate blend of that CAP/HAP bone substitute material.

The invention thus concerns a collagen matrix comprising particles of a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets.

That collagen matrix is useful in particular to form a putty, strip or plug material.

The collagen may be a naturally crosslinked collagen that has been treated by an acidic solution, usually at a pH from 2 to 5. Such a treatment is useful for the wet milling of the collagen in order to get a homogeneous slurry which can then be mixed with the particles of the CAP/HAP bone substitute material, in an acid environment, usually at a pH from 2 to 5, or in an alkaline environment, usually at a pH from 11 to 13. The above procedure allows to give the collagen matrix the moldability and cohesiveness characteristics that are required for a putty.

A suitable naturally crosslinked collagen with a high degree of nativity is described in U.S. Pat. No. 5,837,278. Such a collagen is commercially available under the name Geistlich Bio-Gide® (Geistlich Pharma AG, Switzerland).

The collagen may also be a telopeptide collagen obtained by enzymatic digestion of a native naturally crosslinked collagen with proteolytic enzymes such as trypsin or pepsin.

When the collagen matrix is used as a strip or a plug, the collagen is generally a naturally crosslinked collagen that has been rigidified by physical crosslinking using dehydrothermal treatment (DHT), or, alternatively, by chemical crosslinking, e.g. using EDC/NHS.

Generally, the collagen matrix comprises 60-97 w/w % bone substitute material and 3-40 w/w % collagen, preferably 75-85 w/w % bone substitute material and 15-25 w/w % collagen.

As taught in international PCT patent application WO-2019/115704, the above defined biphasic CAP/HAP bone substitute material shows an excellent capacity to promote bone formation.

Generally, the homogeneous coarse external surface comprises epitactically grown nanocrystalline hydroxyapatite platelets forming an interlocked network of platelets with sizes (width and length) of 0.2 to 20 µm as determined by SEM. The larger the sizes of the platelets, the higher the coarseness of the external surface.

Preferably, the homogeneous coarse external surface comprises epitactically grown nanocrystalline hydroxyapatite platelets forming an interlocked network of platelets with sizes of 0.5 to 5 µm as determined by SEM Usually, that homogeneous coarse external surface comprises epitactically grown hydroxyapatite platelets forming an interlocked network containing pores between 0.03 and 2 µm as determined by Mercury Intrusion Porosimetry (MIP). The higher the pore volume between 0.03 and 2 µm is, the higher is the coarseness of the external surface.

Generally, that homogeneous coarse external surface may be characterized by AFM (Atomic Force Microscopy) with an AFM-derived root mean square roughness ($R_q$) in a range of 50 to 400 nm and an average maximum height of the profile ($R_z$) in a range of 500 to 2000 nm.

Preferably, the homogeneous coarse external surface may be characterized by an AFM-derived root mean square roughness ($R_q$) in a range of 110 to 150 nm and an average maximum height of the profile ($R_z$) in a range of 550 to 750 nm.

Preferably, that percentage of HAP as measured by XRD is from 1.0 to 10.0%, or from 2.0 to 5.0%.

The sintered CAP core comprises tricalcium phosphate (TCP), notably α-TCP (α-$Ca_3(PO_4)_2$) or β-TCP (β-$Ca_3(PO_4)_2$), and/or tetracalcium phosphate (TTCP) $Ca_4(PO_4)_2O$.

According to a frequently used embodiment, the sintered CAP core essentially consists of TCP, α-TCP being preferred.

The epitactically grown layer of nanocrystalline HAP is structurally nearly identical to the natural human bone mineral.

The CAP/HAP bone substitute material may be a particulate or a granulate, the particles or granules having a desired size and shape. Generally, the particles or granules have a size of 250 to 5000 µm, preferably 500 to 2000 µm.

The above collagen matrix may comprise a mixture of particles of the above biphasic CAP/HAP bone substitute material according to international PCT patent application WO-2019/115704 with a low content of HAP (at most 6.0%) which are fast resorbable, thereby promoting new bone formation, and particles of a biphasic CAP/HAP bone substitute material according to EP-B1-2445543 with a high content of HAP (at least 10.0%) which are slowly resorbable, or particles of a material derived from natural bone which is slowly resorbable, such a slowly resorbable material having an osteoconductive effect.

A well-known slowly resorbable material derived from natural bone is Geistlich Bio-Oss® which is manufactured from natural bone by a process described in U.S. Pat. No. 5,167,961 giving a bone mineral retaining substantially the original crystal structure and mineral microstructure of natural bone, while having an organic impurity content below 150 parts per million and a protein content below 135 parts per million. U.S. Pat. No. 5,167,961 is incorporated herein by reference. The phrase "bone mineral retaining substantially the original crystal structure and mineral microstructure of natural bone" includes bone mineral derived according to methods disclosed in U.S. Pat. No. 5,167,961 as well as other bone minerals having crystal structure and mineral microstructure of natural bone.

The invention thus concerns a collagen matrix which comprises:
particles of a biphasic (CAP/HAP) bone substitute material (A) comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets, wherein the % of HAP as measured by XRD is 2.0 to 6.0%, and
particles of a bone substitute material (B) selected from the group consisting of:
a biphasic CAP/HAP bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the % of HAP as measured by XRD is 10 to 40%, or
a bone mineral derived from natural bone and retaining substantially the original crystal structure and mineral microstructure of natural bone, while having an organic impurity content below 150 parts per million and a protein content below 135 parts per million.

Preferably, when that collagen matrix is used as a putty material for posterolateral spinal fusion (PLF):
the % of HAP as measured by XRD is 2.0 to 6.0% in the particles of a CAP/HAP bone substitute material (A) and
the particles of a bone substitute material (B) are particles of a biphasic CAP/HAP bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the % of HAP as measured by XRD is 30 to 40%.

Usually, when that collagen matrix is used as an oral plug material:
the % of HAP as measured by XRD is 2.0 to 6.0% in the particles of a CAP/HAP bone substitute material (A) and
the particles of a bone substitute material (B) are particles of a bone mineral derived from natural bone and retaining substantially the original crystal structure and mineral microstructure of natural bone, while having an organic impurity content below 150 parts per million and a protein content below 135 parts per million.

Generally, the w/w ratio of the particles of a CAP/HAP bone substitute material (A) to the particles of a bone substitute material (B) is from 0.1 to 9.9.

Preferably, when that collagen matrix is used as a putty material for PLF, the w/w ratio of the particles of a CAP/HAP bone substitute material (A) to the particles of a bone substitute material (B) is from 0.4 to 1.0.

Preferably, when that collagen matrix is used as an oral plug material, the w/w ratio of the particles of a CAP/HAP bone substitute material (A) to the particles of a bone substitute material (B) is from 0.8 to 4.

Generally, that collagen matrix is prepared by a process comprising dispersing collagen fibres of a native naturally crosslinked collagen into an acidic solution at a pH from 2 to 5 or into a basic solution at a pH from 11 to 13 such as to produce a collagen slurry, mixing that collagen slurry with the above biphasic CAP/HAP bone substitute material and homogenizing.

The collagen—CAP/HAP slurry is then usually freeze-dried and sterilized by gamma-ray or X-ray irradiation, or ethylene oxide treatment.

Prior to implantation, the lyophilized and sterilized putty is generally rehydrated with blood or an isotonic saline solution.

The invention also concerns a process of preparing the above collagen matrix for use as a putty material, comprising dispersing collagen fibres of a native naturally cross-linked collagen into an acidic solution at a pH from 2 to 5 such as to produce a collagen slurry, mixing and homogenizing that collagen slurry with particles of the above biphasic CAP/HAP bone substitute material, such as to produce a collagen-CAP/HAP slurry, freeze-drying that slurry and sterilizing by gamma-ray or X-ray irradiation or ethylene oxide treatment.

Preferably, the acidic collagen slurry is wet milled in a colloidal mill, blender mill or cutter mill.

The invention also concerns a granulate blend, in particular for use a bone substitute material, which is a mixture of particles of the above biphasic CAP/HAP bone substitute material according to international PCT patent application WO-2019/115704 with a low content of HAP (at most 6.0%) which are fast resorbable, thereby promoting new bone formation, and particles of a biphasic CAP/HAP bone substitute material according to EP-B1-2445543 with a high content of HAP (at least 10.0%) which are slowly resorbable or particles of a material derived from natural bone which is slowly resorbable, such a slowly resorbable material having an osteoconductive effect.

A well-known slowly resorbable material derived from natural bone is Geistlich Bio-Oss® which is manufactured from natural bone by a process described in U.S. Pat. No. 5,167,961 giving a bone mineral retaining substantially the original crystal structure and mineral microstructure of natural bone, while having an organic impurity content below 150 parts per million and a protein content below 135 parts per million.

The invention thus concerns a granulate blend which comprises:
particles of a a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets, wherein the % of HAP as measured by XRD is 2.0 to 6.0%, and particles of a bone substitute material (B) selected from the group consisting of:
a biphasic CAP/HAP bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the % of HAP as measured by XRD is 10 to 40%, or a bone mineral derived from natural bone and retaining substantially the original crystal structure and mineral microstructure of natural bone, while having an organic impurity content below 150 parts per million and a protein content below 135 parts per million.

Preferably, in that granulate blend:
the % of HAP as measured by XRD is 2.0 to 6.0% in the particles of a CAP/HAP bone substitute material (A) and the particles of a bone substitute material (B) are particles of a biphasic CAP/HAP bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the % of HAP as measured by XRD is 30 to 40%.

Generally, the w/w ratio of the particles of a CAP/HAP bone substitute material (A) to the particles of a bone substitute material (B) is from 0.1 to 9.9.

BRIEF DESCRIPTION OF THE DRAWINGS

The invention will be described in further detail hereinafter with reference to illustrative examples of preferred embodiments of the invention and the accompanying drawing figures, in which.

All SEM pictures of FIG. 1 and FIGS. 2A-2E have a magnification of 3500.

Figure 3A:
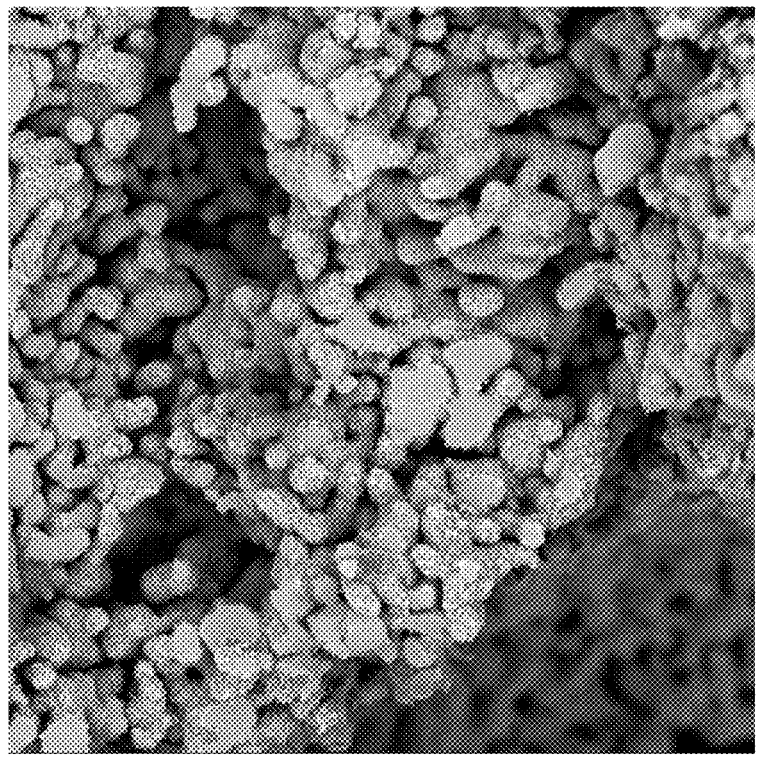

FIG. 3A represents a SEM picture of a cross-section of prototype 5 (40% ethanol, 1-2 mm granule) at low magnification (1000×). The bottom-right corner shows the outer surface of the granule and the center of the granule is located towards the top-left corner.

Figure 3B:
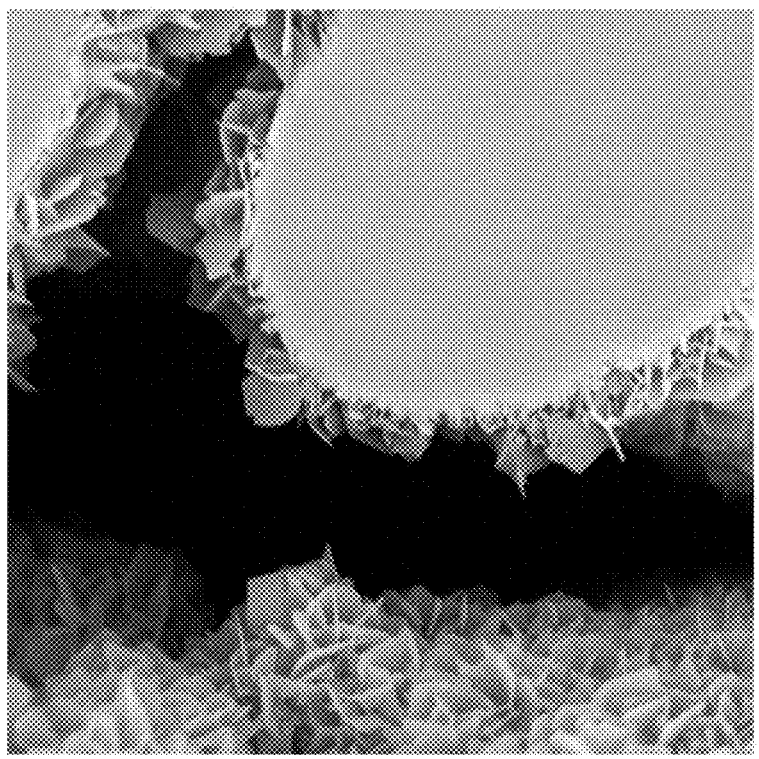

FIG. 3B represents a SEM picture of a cross-section of prototype 5 (40% ethanol, 1-2 mm granule) at higher magnification (14,000×).

FIG. 4 represents SEM pictures (the two upper pictures) and AFM pictures (the other four pictures) of prototypes 3a (left: 20% ethanol) and 6a (right: 50% ethanol) of non-porous discs of bone substitute materials according to the invention prepared in Example 2.

FIGS. 5A-5B represent the osteocalcin (OCN, FIG. 5A) and the osteopontin (OPN, FIG. 5B) responses of fetal human mesenchymal stem cells (hMSCs) in contact with bone substitute materials according to the invention compared to prior art bone substitute materials in an in vitro test.

Figure 6:
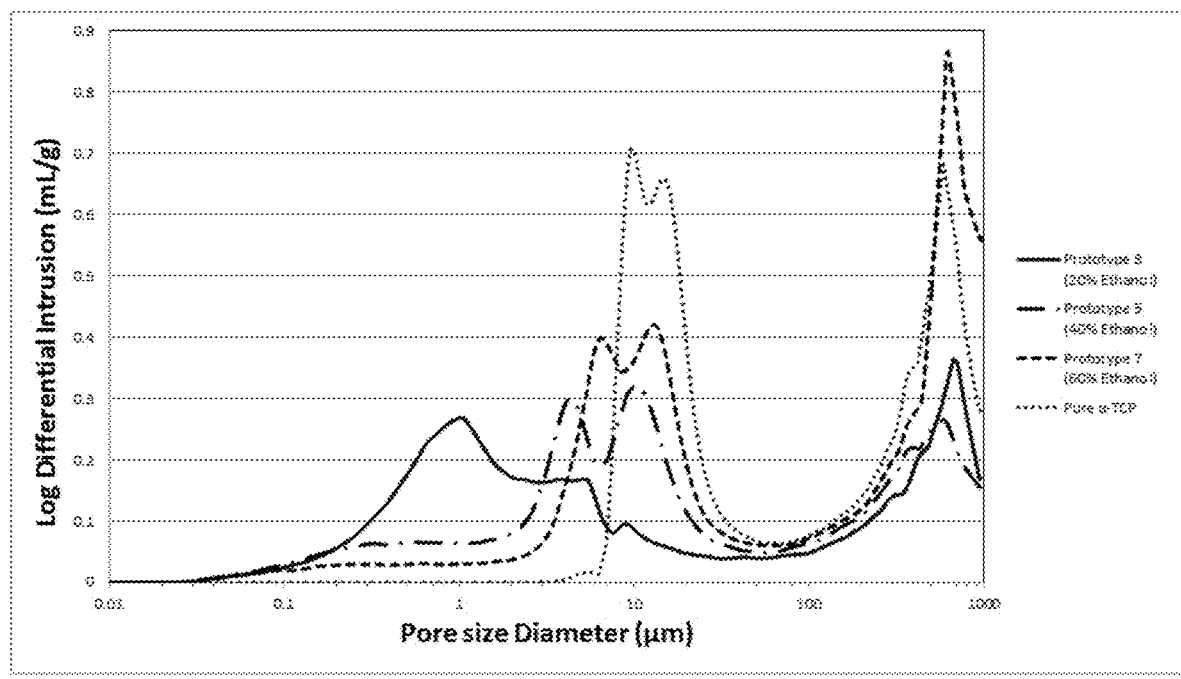

FIG. 6 represents MIP diagrams of 1-2 mm granules of prototypes 3 (20% ethanol), 5 (40% ethanol) and 7 (60% ethanol) of the 1-2 mm granules of bone substitute materials according to the invention prepared in Example 2 and pure σ-TCP produced as described in Example 1.

Figure 7:
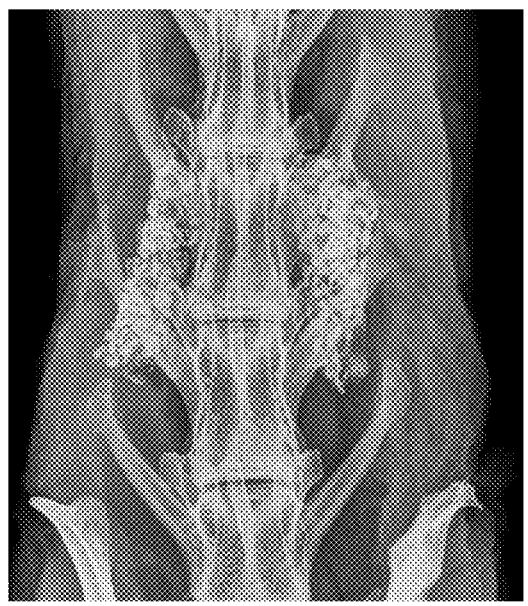

FIG. 7 represents a rabbit spine radiograph 12 weeks after implantation of the collagen matrix putty prototype according to the invention prepared in Example 6 3).

Figure 8:
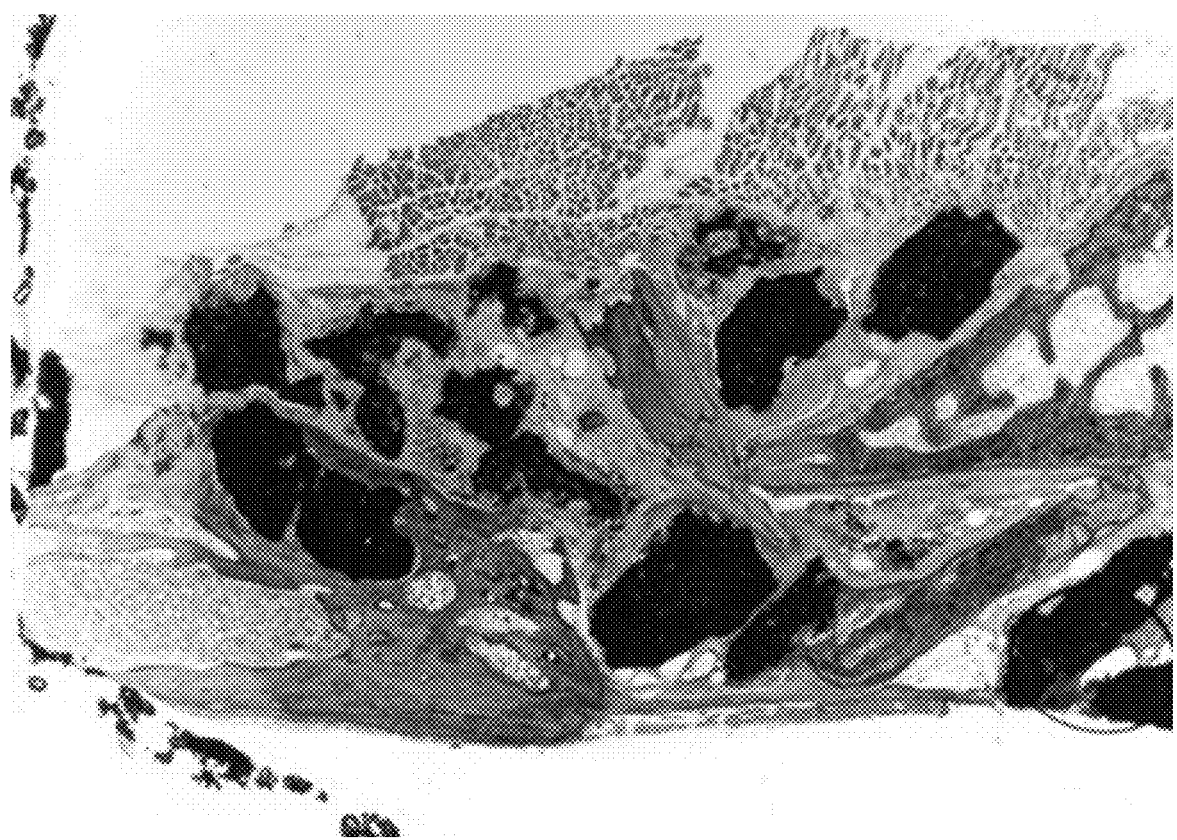

FIG. 8 represents a resin histology fluorescence microscopy photograph of a PLF procedure in a rabbit with the collagen matrix putty prototype according to the invention prepared in Example 6 3) 12 weeks after implantation.

DETAILED DESCRIPTION OF THE INVENTION

The following examples illustrate the invention without limiting its scope.

Example 1 Preparation of Biphasic Calcium Phosphate/Hydroxyapatite (CAP/HAP) Bone Substitute Materials According to EP-B1-2445543

A bulk sintered material of alpha-TCP, porous granules thereof with a particle size of 1.0-2.0 mm and transformed granules having an epitactically grown HAP coating were prepared similarly to Examples 1, 2 and 4 of EP-B1-2445543. 364 g dicalcium phosphate anhydrous powder, 136 g calcium carbonate powder and 220 ml deionized water were mixed for 5 min at 700 rpm using a laboratory stirrer. The slurry from the mixing process was immediately transferred into a high temperature stable platinum cup. The filled platinum cup was placed in a cold furnace. The furnace was heated to 1400° C. by using a heating rate of 100° C. per hour. This temperature was kept for 12 hours and afterwards the furnace was cooled down to 800° C. with a cooling rate of 500° C. per hour, then cooled down to 300° C. with a cooling rate of 125° C. per hour and finally cooled down to room temperature by switching of the furnace. The bulk sintered material (phase pure α-Ca$_3$(PO$_4$)$_2$) was removed from the furnace and the platinum cup. The control of phase purity was performed using powder X-ray diffraction analysis.

The bulk product was crushed by using a jaw crusher (jaw distances varied from 10 to 1 mm). The produced granules were sieved by using a sieving machine and sieve inserts with mesh apertures of 2 mm and 1 mm. After sieving, the granules were rinsed with ethanol for separating fine powder residuals adsorbed to the granules. The porous granules were dried for 1 h at 80° C. in a cabinet dryer. The cleanness of the particle surfaces after rinsing was controlled by surface observation using scanning electron microscopy.

A buffered solution adequate for the coating and phase transformation process was prepared by dissolving 0.4 mol/l sodium dihydrogen phosphate (NaH$_2$PO$_4$) in distilled water. The pH of the solution was adjusted to 7.45 at room temperature by using sodium hydroxide (NaOH). The granules produced according to the previous paragraphs were immersed into the prepared solution and stored within a well-tempered water bath (40° C.) for 30 min (prototype 1) respectively 40 min (prototype 2). After immersing, the granules were rinsed 3 times with distilled water to stop the phase transformation process and remove residuals from the buffered solution. The porous granules were dried at 100° C. in a cabinet dryer for 2 hours. SEM with a magnification of 3500× was performed on granules of prototype 1 and prototype 2.

Figure 1A:
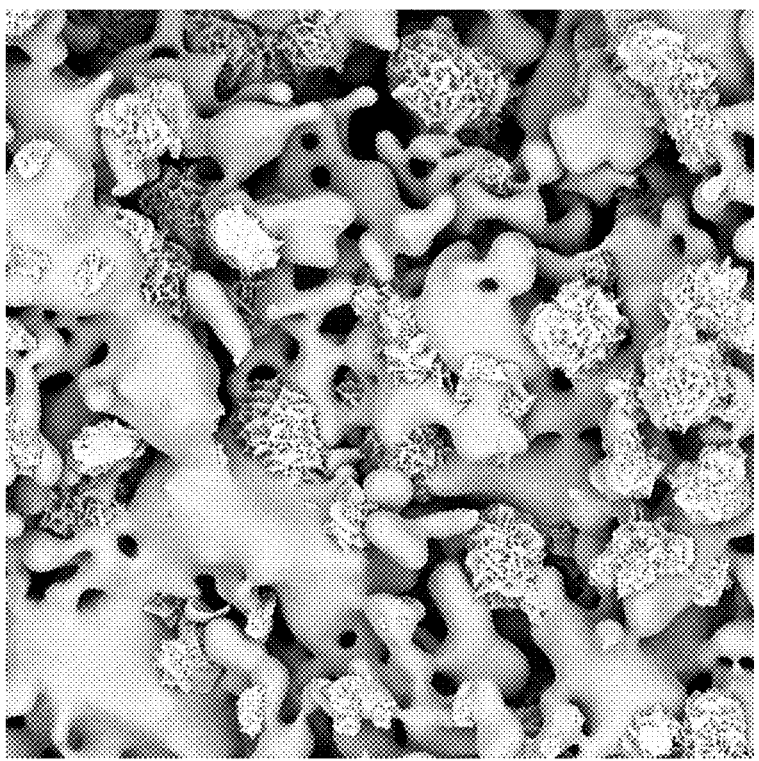
FIG. 1A represents a SEM picture of prototype 1 (1-2 mm granule) of a bone substitute material disclosed by EP-B1-2445543 and prepared in Example 1 having a transformation time of 30 min wherein the smooth areas represent about 70% of the total external surface as measured by SEM.
Figure 1B:
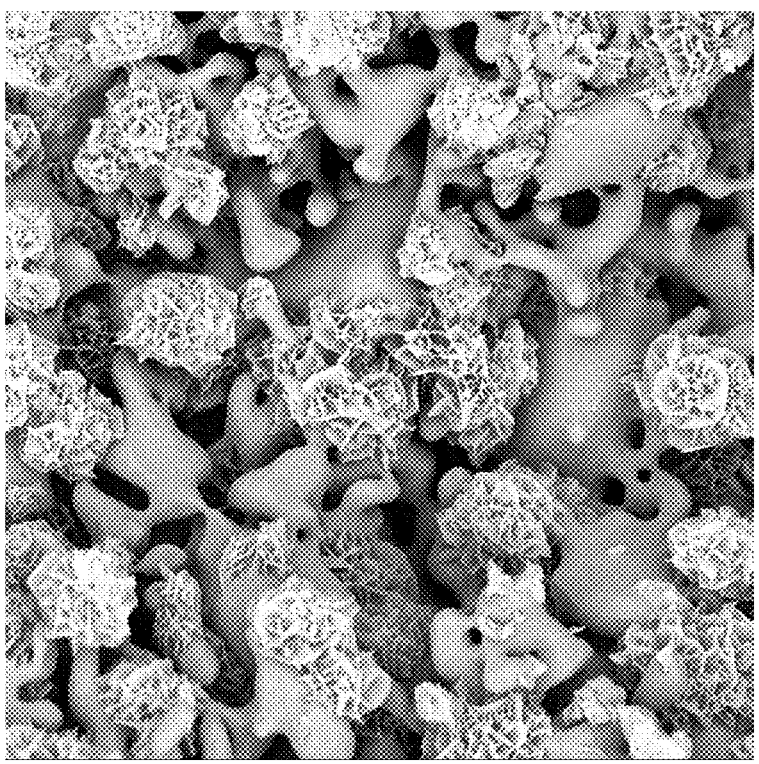
FIG. 1B which represents an SEM picture of prototype 2 (1-2 mm granule) of a bone substitute material disclosed by EP-B1-2445543 and prepared in Example 1 having a transformation time of 40 min wherein the smooth areas represent about 50% of the total external surface as measured by SEM.
Figure 2A:
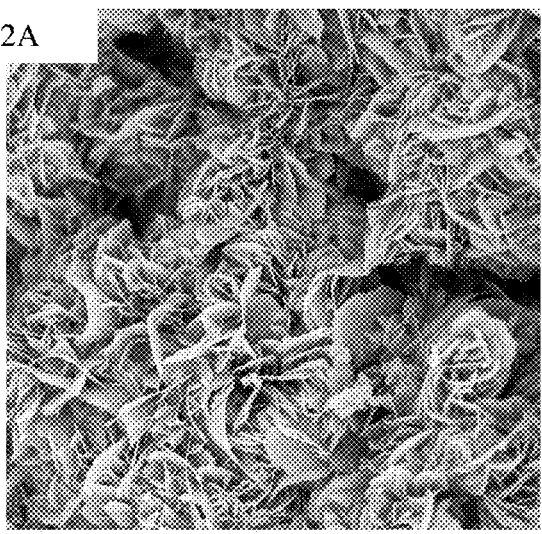
FIGS. 2A-2E represent SEM pictures of prototype 3 (FIG. 2A): 20% ethanol, 1-2 mm granule), prototype 4 (FIG. 2B): 30% ethanol, 1-2 mm granule), prototype 5 (FIG. 2C): 40% ethanol, 1-2 mm granule), prototype 6 (FIG. 2D): 50% ethanol, 1-2 mm granule) and prototype 7 (FIG. 2E): 60% ethanol, 1-2 mm granule) of bone substitute materials according to the invention.
Figure 2B:
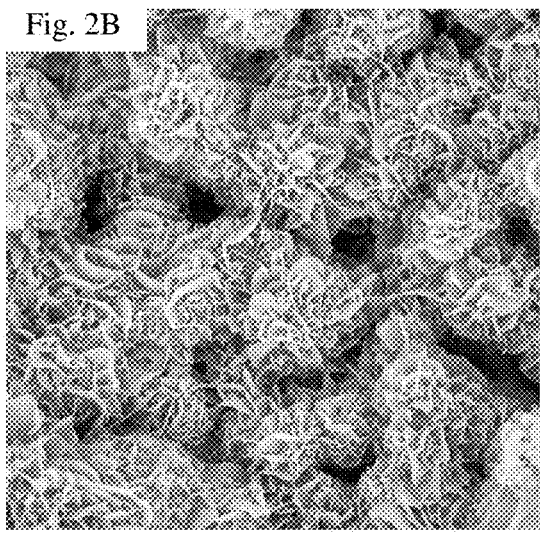
Figure 2C:
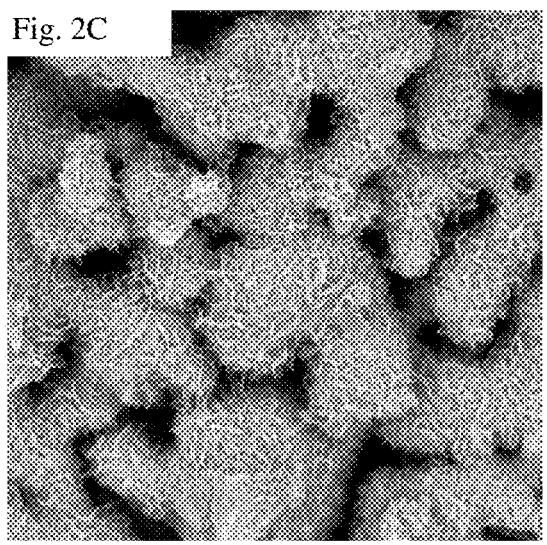
Figure 2D:
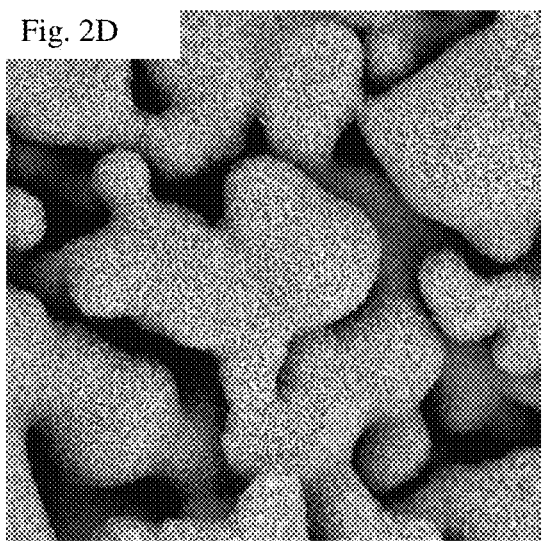
Figure 2E:
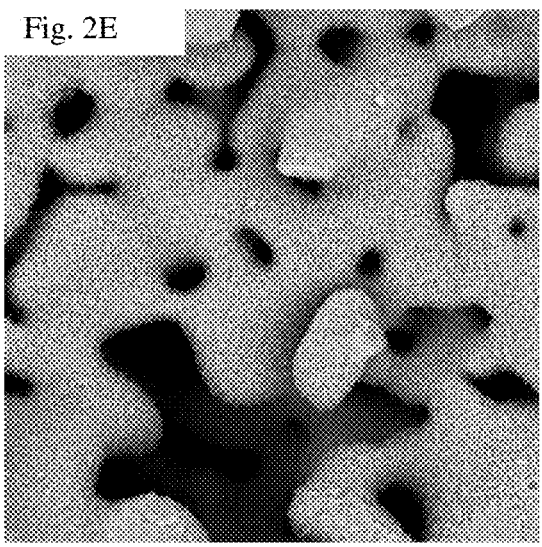

As apparent from FIGS. 1A and 1B, which represent SEM pictures of prototypes 1 and 2, the external surface of the granules is non-homogeneous comprising individual (separated) clusters of flat crystal platelets consisting of epitactically grown HAP nanocrystals and smooth areas between the crystals.

By measuring the surface occupied by the individual clusters and the smooth areas on the SEM pictures for each of prototype 1 and prototype 2, it was determined that the smooth areas represent about 70% of the external surface for prototype 1 and about 50% of the external surface for prototype 2.

Example 2 Preparation of Biphasic Calcium Phosphate/Hydroxyapatite (CAP/HAP) Bone Substitute Materials According to the Invention of International PCT Patent Application WO-2019/115704

1) Preparation of Granules of Bone Substitute Material 1-2 mm sized porous granules of phase pure α-TCP were produced as described in above Example 1.

The phase transformation and coating step was performed in glass flasks placed in a water bath set to 40° C. The transformation buffer was an aqueous solution of sodium dihydrogen phosphate (NaH$_2$PO$_4$) mixed with different proportions of ethanol. The molarity of the aqueous solution of sodium dihydrogen phosphate was varied between 0.05 M and 0.3M and the content of ethanol between 20 and 60 w/w %. The pH of the transformation solution was between 7.3 and 7.6.

The glass flasks were filled with the transformation buffer and alpha-TCP granules were added with a ratio between 1:40 to 1:80 (granules to transformation solution). The granules were immersed in the transformation solution at 40° C. for a period between 24 and 72 hours. After immersing, the granules were rinsed 5 times with deionised water (granules to water ratio being 1:10 with respect to weight) and 2 times with Ethanol (99.9%, granules to ethanol ratio being 1:10 with respect to weight) to stop the phase transformation process and remove residuals from the buffered solution. The porous granules were dried at 100° C. in a cabinet dryer for 2 hours.

The surface morphology after the coating and phase transformation process was observed using SEM.

FIGS. 2A-2E represents SEM pictures with a 3500× magnification of prototype 3 (20% ethanol), prototype 4 (30% ethanol), prototype 5 (40% ethanol), prototype 6 (50% ethanol) and prototype 7 (60% ethanol) of bone substitute materials according to the invention. It can be seen by comparing FIGS. 1A and 1B to FIGS. 2A-2E, that the non-homogeneous external surface of prototypes 1 and 2 with the individual clusters of flat crystal platelets and smooth areas in between is replaced by a homogeneous coarse external surface without any individual crystal clusters. The homogeneous coarse external surface is built up of an interlocked network of epitactically grown hydroxyapatite platelets. The individual platelet sizes are decreased by increasing the ethanol content in the transformation solution as observed by the SEM analysis thus decreasing the coarseness or roughness of the external surface.

FIG. 3A represents a SEM picture of a cross-section of prototype 5 (40% ethanol, 1-2 mm granule) at low magnification (1000×). The bottom-right corner shows the outer surface of the granule and the center of the granule is located towards the top-left corner.

FIG. 3B represents a SEM picture of a cross-section of prototype 5 (40% ethanol, 1-2 mm granule) at higher magnification (14,000×) where one can clearly see the individual flat crystal platelets which are the building blocks of the coarse surface. There is no difference between the coarse external surface in the center of the granule and the coarse external surface on the outer surface of the granule.

Determination of the Pore Size Distribution by Mercury Intrusion Porosimetry (MIP)

The pore size distribution of the granules was determined using mercury intrusion porosimetry (MIP). MIP is a standard characterization technique used to determine the pore size distribution of porous materials. The technique is well known in the art and is for example described in Gregg, S. J. and Sing, K. S. W., Adsorption, Surface Area and Porosity, 2nd ed., Academic Press Inc. (1982), 173-190.

FIG. 6 represents MIP diagrams of prototypes 3, 5 and 7 of bone substitute materials according to the invention compared to pure α-TCP (produced according to example 1 and core material of the prototypes 3, 5 and 7). All measurements were performed with 1-2 mm granules.

It can be seen that the pure α-TCP sample does not have any pores in the range of 0.03 to 2 µm because of its smooth surface. All the bone substitute materials according to the invention contain pores in the range of 0.03 to 2 µm due to the porous nature of the homogeneous coarse external surface which is built up of an interlocked network of epitactically grown hydroxyapatite platelets. The pore volume of the coarse external surface, which corresponds to the area under the MIP curve in the range of 0.03 to 2 µm, depends on the individual platelet sizes of the interlocked network. The bigger the individual platelets are, the higher is the included pore volume of the interlocked network. Thus, the included pore volume of the interlocked network can directly be correlated to the coarseness of the surface. The higher the pore volume in the range of 0.03 to 2 µm in the MIP diagram is, the higher is the coarseness of the surface. Prototype 3 has the largest pore volume (area under the curve) in the range of 0.03 to 2 µm of the shown prototypes, followed by prototype 5 and 7. It is confirmed by the SEM analysis in FIGS. 2A-2E that the coarseness of the prototypes is decreasing from prototype 3 to prototype 5 and 7.

2) Preparation of Non-Porous Discs of Bone Substitute Material

The 1-2 mm sized granules of phase pure α-TCP produced as described in above Example 1 were milled with a planetary mill during 20 hours with 150 rpm to obtain a fine powder. The fine powder was filled in a pressing mold and compacted with a hand press with a load of 1 ton. The green body was removed from the mold and transferred to a high temperature furnace. The furnace was heated to 1450° C. by using a heating rate of 250° C. per hour. This temperature was kept for 24 hours and afterwards the furnace was cooled down to 800° C. with a cooling rate of 500° C. per hour and then cooled down to room temperature with a cooling rate of 150° C. per hour. The bulk sintered non-porous material (phase pure α-$Ca_3(PO_4)_2$) was removed from the furnace. The control of phase purity was performed using powder X-ray diffraction analysis and the surface characteristics were analysed by using SEM. The phase transformation and coating of the prepared discs was performed as described above under 1), with the only difference that the weight ratio of α-TCP to transformation solution was 1 to 3.5.

Prototypes 3a (20% ethanol) and 6a (50% ethanol) of bone substitute materials according to the invention were thus prepared.

The surface morphology after the coating and phase transformation process was observed using SEM. The corresponding roughness parameters were determined using atomic force microscopy AFM.

The SEM images in FIG. 4 confirm that the morphology of the homogeneous coarse external surface of the non-porous discs is identical to the coarse external surface of the granules produced with the corresponding ethanol content from Example 2 paragraph 1 (prototypes 3 and 3a and prototypes 6 and 6a).

Atomic Force Microscopy (AFM)

Surface measurements at the nanoscale were evaluated using atomic force microscopy (TT-AFM, AFM Workshop) in tapping mode. AFM analyses were conducted under ambient atmosphere using non-porous cylindrical discs with a diameter of 11 mm and a height of 1 mm. A resonance frequency of 190 kHz and a tip radius of up to 10 nm were used. Each AFM analysis was performed over a 50 µm×50 µm area and three samples of every group were scanned. The original data was plane-leveled to remove tilt by applying a numerical correction and mean values of root mean square roughness ($R_q$) and average maximum height of the profile ($R_z$) were determined using the Gwyddion software.

A similar surface characterization of the surface is for example described in US-2013-0045360-A1.

FIG. 4 represents AFM pictures of the prototypes 3a (20% ethanol, left hand side) and 6a (50% ethanol, right hand side) of non-porous discs prepared according to the invention. The AFM-derived roughness values for the prototypes 3a and 6a can be found in following Table 1.

TABLE 1

AFM derived roughness values for prototypes 3a and 6a.

|  | $R_q$ [nm] | $R_z$ [nm] |
| --- | --- | --- |
| Prototype 3a (20% Ethanol) | 237 ± 31 | 1391 ± 194 |
| Prototype 6a (50% Ethanol) | 130 ± 13 | 630 ± 82 |

As seen in Table 1, the mean value of the root mean square roughness ($R_q$) decreased from 237 nm to 130 nm and the average maximum height of the profile ($R_z$) decreased from 1391 nm to 630 nm by increasing the ethanol content from 20% to 50%.

Example 3 In Vitro Test of Osteogenic Differentiation of Fetal Human Mesenchymal Stem Cells (hMSCs)

To assess if the bone substitute material prototypes prepared in Examples 1 and 2 support osteogenic differentiation, about 200,000 hMSCs isolated from a human fetal femur after 22 weeks of gestation (commercially available from ScienCell: Cat#7500, Lot#6890) were seeded on 320 mg granules of those bone substitution material prototypes and cultivated for three weeks. The first seven days of culture the commercially available hMSCs expansion medium (MSCM Medium, Cat#7501, ScienCell) was used to optimally support cell proliferation. For the following 14 days the medium was changed to DMEM complemented with 10% FBS and Penicillin/Streptomycin. No additional osteogenic agents were added to the cell culture medium. After three weeks of hMSCs cultivation, total mRNA was isolated, transcribed into cDNA and Real Time Quantitative PCR was performed. The gene expression was calculated after the ΔΔCT method (see Livak K. J. and Schmittgen T. D., Analysis of relative gene expression data using real time quantitative PCR and the 2-ΔΔCT method, 2001, Methods 25, pp. 402-408) using GAPDH as a house-keeping gene. The expression of the osteogenic differentiation markers osteopontin (OPN) and osteocalcin (OCN) was measured for all bone substitute material prototypes in granular form (1-2 mm) prepared in Examples 1 and 2. Those measurements showed a significantly higher expression of osteogenic differentiation markers OPN and OCN for the bone substitute material prototypes according to the invention of Example 2 than for the prior art bone substitute material prototypes of Example 1 (see FIGS. 5A-5B).

Based on these in vitro results an enhanced osteogenic response for the bone substitute material prototypes according to this invention is to be expected in vivo.

Example 4 Comparison of the Crystal Size and Morphology for the HAP Nanocrystals of the Biphasic CAP/HAP Bone Substitute Material of the Invention of International PCT Patent Application WO-2019/115704 and Human Bone Mineral Crystal size analysis was performed by using as in EP-B1-2445543 a refinement of X-ray diffraction data by applying the Bragg method on samples of prototype 3 and on natural human bone mineral. invention and human bone mineral have the same morphology and the same crystal size.

See Table 2 below.

TABLE 2

Comparison of the HAP crystal size and morphology for the CAP/HAP bone substitute of the invention and human bone mineral

| Crystallographic axes (hexagonal space group $P6_3/m$) | CAP/HAP of the invention prepared at physiological temperature. Crystal size$^+$ [nm] | natural human bone mineral Crystal size$^+$ [nm] |
|---|---|---|
| a (1, 0, 0) | 18 (±4) | 15-21 |
| b (0, 1, 0) | 18 (±4) | 15-21 |
| c (0, 0, 1) | 38 (±8) | 34-45 |

Example 5 Preparation of a Collagen Matrix According to the Invention Comprising Particles of a CAP/HAP Bone Substitute Material Containing 3.0 w/w % HAP According to International PCT Patent Application WO-2019/115704

1) Preparation of a Fast-Resorbing Biphasic CAP/HAP Bone Substitute Material Containing 3.0 w/w % HAP 0.5-2 mm sized porous granules of biphasic calcium phosphate/hydroxyapatite (CAP/HAP) bone substitute material were produced according to international PCT patent application WO-2019/115704 by a process close to that described in Example 2 above. The transformation buffer was a 0.1M solution of sodium dihydrogen phosphate ($NaH_2PO_4$) containing 50% ethanol. The content of HAP coming from the surface transformation as measured by XRD was 3.0 w/w %.

2) Preparation of a Collagen Matrix According to the Invention for Use as a Putty A selected amount of collagen fibers (3 w/w %) were dispersed in deionized water. The source of the collagen fibers to produce the putty material was the same as in the commercially available product Geistlich Bio-Gide® from Geistlich Pharma AG. Subsequently, the pH value of the slurry was adjusted with a 2M solution of hydrochloric acid to pH=3.5. Then, the slurry was wet-milled using a colloidal mill. In a next step, the granules of biphasic CAP/HAP bone substitute material prepared in 1) above were added to the collagen slurry with a ratio of 80 w/w % bone substitute material and 20 w/w % collagen. The slurry was homogenized after adding the bone substitute material by hand with a spatula. Then, the slurry was filled into metal molds (23 mm×23 mm×6 mm) and afterwards lyophilized (freezing to −40° C., primary drying at −5° C. and 300 μbar for 24 h, secondary drying at 20° C. and 10 μbar for 11 h). The lyophilized material was sterilized with x-ray radiation.

A putty prototype with good handling properties was obtained by rehydration with blood or an isotonic saline solution.

Procedure for Assessing the Handling Properties of the Putty Prototypes:

The putty materials were brought in contact with a specific amount of heparinized blood and afterwards the testing protocol included the following steps:
1. Wettability: The foam can be wetted with heparinized blood within 4 min (without manipulation).
2. Squeezing: Additional blood can be squeezed out.
3. Stickiness: The putty mass does not stick to gloves or instruments.
4. Cohesion: The putty is cohesive and does not fall apart.
5. Moldability: The moldable putty can easily be formed into the desired shape (ball as most challenging form).
6. Pressure resistance: The material was not pushed to the side when applying pressure.

3) Preparation of a Collagen Matrix According to the Invention for Use as a Strip or a Plug The lyophilized material obtained in 2) of this Example above was submitted to a dehydrothermal treatment (DHT) at 0.1-10 mbar and 80-140° C. for 12-96 hours. To obtain the plug material, the metal molds in 2) of this Example were of cylindrical or conical shape with a diameter of 8 to 12 mm and a depth of 8 to 16 mm.

Example 6 Preparation of a Collagen Matrix Comprising a Mixture of Particles of a CAP/HAP Bone Substitute Material According to International PCT Patent Application WO-2019/115704 Containing 3.0 w/w % HAP and Particles of a CAP/HAP Bone Substitute Material According to EP-B1-2445543 Containing 35 w/w % HAP 1) Preparation of a Slow-Resorbing Biphasic CAP/HAP Bone Substitute Material According to EP-B1-2445543 Containing 35% HAP 0.5-2 mm sized porous granules of the biphasic calcium phosphate/hydroxyapatite (CAP/HAP) bone substitute material were produced according to the process described in EP-B1-2445543. The transformation buffer was a 0.15M solution of sodium dihydrogen phosphate (NaH$_2$PO$_4$) with a pH of 7.45±0.1. The alpha-TCP granules were immersed in the transformation solution at 40° C. for 24 hours. After the surface transformation, the granules were washed and dried in a cabinet dryer. The content of HAP coming from the surface transformation as measured by XRD was 35 w/w %.

2) Preparation of a Granulate Blend, Mixture of Fast-Resorbing and Slow-Resorbing Particles of Biphasic Bone Substitute Material 0.5-2 mm sized porous particles of the biphasic CAP/HAP bone substitute material according to international PCT patent application WO-2019/115704 containing 3.0 w/w % HAP prepared in Example 5 under 1), and 0.5-2 mm sized porous particles of the biphasic CAP/HAP bone substitute material according to EP-B1-2445543 containing 35% w/w HAP prepared in this Example under 1) above were mixed in a w/w ratio of 40:60. The granulate blend was homogenized in a turbula shaker mixer.

3) Preparation of a Collagen Matrix According to the Invention for Use as a Putty A selected amount of collagen fibers of Geistlich Bio-Gide® (3 w/w %) were dispersed in deionized water. Subsequently, the pH value of the slurry was adjusted with a 2M solution of hydrochloric acid to pH=3.5. Then, the slurry was wet-milled using a colloidal mill. In a next step, the granulate blend of biphasic CAP/HAP bone substitute material prepared in this example under 2) above was added to the collagen slurry with a ratio of 80 w/w % bone substitute material and 20 w/w % collagen. The slurry was homogenized after adding the bone substitute material by hand with a spatula. Then, the slurry was filled into metal molds (23 mm×23 mm×6 mm) and afterwards lyophilized (freezing to −40° C., primary drying at −5° C. and 300 µbar for 24 h, secondary drying at 20° C. and 10 µbar for 11 h). The material was then sterilized with X-ray radiation.

4) Preparation of a Collagen Matrix According to the Invention for Use as a Strip or a Plug The lyophilized material obtained in 3) of this Example above was submitted to a dehydrothermal treatment (DHT) at 0.1-10 mbar and 80-140° C. for 12-96 hours. To obtain the plug material, the metal molds in 3) of this Example were of cylindrical or conical shape with a diameter of 8 to 12 mm and a depth of 8 to 16 mm.

Example 7 Testing of a Putty According to the Invention in a Rabbit Posterolateral Spinal Fusion (PLF) Model The collagen matrix obtained in Example 6 3) above was tested as a putty in the rabbit PLF model disclosed by W. R. Walsh et al., 2009, Eur. Spine J. 18:1610-1620, comparatively to the Mastergraft™ putty (biphasic calcium phosphate granules in a collagen matrix, marketed by Medtronic) and the Actifuse ABX putty (Si-substituted hydroxyapatite in poloxamer matrix, marketed by Baxter).

The fused mass was radiologically clearly visible for each of those putties 12 weeks after implantation. The Mastergraft putty showed a higher degradation rate.

See FIG. 7 where the fusion mass is clearly visible for the putty according to the invention.

As shown in FIG. 8, the particles of the biphasic CAP/HAP bone substitute material containing 3.0 w/w % HAP resorbed more quickly than the particles of the biphasic CAP/HAP bone substitute material containing 35% w/w HAP (which appear bigger in size and more uniform in shape in FIG. 8), providing space for the ingrowth of new bone New bone formation across the defect can be observed in FIG. 8.

Any patent, patent publication, publication, or other disclosure material mentioned above is incorporated by reference herein for any and all purposes.

While various embodiments of the present invention have been shown and described, further modifications of the methods and materials described herein may be accomplished by appropriate modifications by one of ordinary skill in the art without departing from the scope of the present invention. Several such potential modifications have been mentioned, and other modifications will be apparent to those skilled in the art. For example, the examples, embodiments, geometries, materials, dimensions, ratios, steps, etc, discussed above are illustrative and not required. The scope of the present invention should, therefore, be considered in terms of the following claims and is understood not to be limited to the details of structure and operation shown and described in the specification and drawings.

The invention claimed is:

1. A collagen matrix comprising collagen and particles of a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets, wherein the homogeneous coarse external surface comprises epitactically grown nanocrystalline hydroxyapatite platelets forming an interlocked network of platelets with sizes of 0.2 to 20 µm as determined by Scanning Electron Microscopy (SEM), wherein the collagen matrix comprises 75-80 w/w % bone substitue material and 15-25 w/w % collage.

2. The collagen matrix of claim 1, wherein the collagen is a naturally crosslinked collagen that has been treated by an acidic solution.

3. The collagen matrix of claim 1, wherein the collagen is a naturally crosslinked collagen that has been physically crosslinked by dehydrothermal treatment (DHT) or chemically crosslinked.

4. A collagen matrix of claim 1, wherein in the biphasic calcium phosphate/hydroxyapatite (CAP/HAP) bone substitute material the coarse surface comprises epitactically grown nanocrystalline hydroxyapatite platelets forming an interlocked network of platelets with sizes of 0.5 to 5 µm as determined by Scanning Electron Microscopy (SEM).

5. The collagen matrix of claim 1, wherein in the biphasic calcuim phosphate/hydroxyapatite (CAP/HAP) bone substite material, the homogeneous coarse external surface comprises epitactically grown hydroxyapatite platelets forming an interlocked network containing pores between 0.03 and 2 µm as determined by Mercury Intrusion Porosimetry (MIP).

6. The collagen matrix of claim 1, wherein in the biphasic calcium phosphate/hydroxyapatite (CAP/HAP) bone substitute material, the homogeneous coarse external surface is characterized by Atomic Force Microscopy (AFM) with an AFM-derived root mean square roughness $R_q$ in a range of 50 to 400 nm and an average maximum height of the profile $R_z$ in a range of 500 to 2000 nm.

7. The collagen matrix of claim 1, wherein, in the biphasic calcium phosphate/hydroxyapatite (CAP/HAP) bone substitute material, the percentage of HAP is from 1.0 to 10.0% as measured by XRD.

8. The collagen matrix of claim 1, which comprises:
collagen and particles of a CAP/HAP bone substitute material (A) comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets, wherein the % of HAP as measured by XRD 2.0 to 6.0%, wherein the homogeneous coarse external surface comprises epitactically grown nanocrystalline hydroxyapatite platelets forming an interlocked network of platelets with sizes of 0.2 to 20 µm as determined by Scanning Electron Microscopy (SEM), and
particles of a bone substitute material (B) selected from the group consisting of:
a biphasic CAP/HAP bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the % of HAP as measured by XRD is 10 to 40%, and
a bone mineral derived from natural bone and retaining original crystal structure and mineral microstructure of natural bone, while having an organic impurity content below 150 parts per million and a protein content below 135 parts per million.

9. The collagen matrix of claim 8, wherein
the % of HAP as measured by XRD is 2.0 to 6.0% in the particles of a CAP/HAP bone substitute material (A), and
the particles of a bone substitute material (B) are particles of a biphasic CAP/HAP bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the % of HAP as measured by XRD is 30 to 40%.

10. The collagen matrix of claim 8, wherein
the % of HAP as measured by XRD is 2.0 to 6.0% in the particles of a CAP/HAP bone substitute material (A) and
the particles of a bone substitute material (B) are particles of a bone mineral derived from natural bone and retaining substantially the original crystal structure and mineral microstructure of natural bone, while having an organic impurity content below 150 parts per million and a protein content below 135 parts per million.

11. The collagen matrix of claim 8, wherein the w/w ratio of the particles of a CAP/HAP bone substitute material (A) to the particles of a bone substitute material (B) is from 0.1 to 9.9.

12. The collagen matrix of claim 8, wherein the particles of the CAP/HAP bone substitute material (A) have a w/w ratio of 0.4 to 1.0 to the particles of the bone substitute material (B).

13. A granulate blend comprising a mixture of:
granules of a biphasic (CAP/HAP) bone substitute material (A) comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets, wherein the % of HAP as measured by XRD is 2.0 to 6.0%, wherein the homogeneous coarse external surface comprises epitactically grown nanocrystalline hydroxyapatite platelets forming an interlocked network of platelets with sizes of 0.2 to 20 µm as determined by Scanning Electron Microscopy (SEM), and
granules of a bone substitute material (B) selected from the group consisting of:
a biphasic CAP/HAP bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the % of HAP as measured by XRD is 10 to 40%, and
a bone mineral derived from natural bone and retaining original crystal structure and mineral microstructure of natural bone, while having an organic impurity content below 150 parts per million and a protein content below 135 parts per million.

14. The granulate blend of claim 13, wherein the w/w ratio of the particles of a CAP/HAP bone substitute material (A) to the particles of a bone substitute material (B) is from 0.1 to 9.9.

15. The granulate blend of claim 13, wherein the granules have a diameter of 250 to 5000 µm.

16. A method of promoting bone formation, bone regeneration and/or bone repair at a defect site in a subject by implanting the granulate blend of claim 13 at the defect site, such that bone formation, bone regeneration and/or bone repair are promoted at the defect site.

17. A method of promoting osteogenic differentiation in a bone of a subject, comprising administering the granulate blend of claim 13 to the bone of a subject, such that osteogenic differentiation is promoted in the bone of the subject.

18. A process of preparing a putty material comprising the collagen matrix of claim 1, comprising
a) dispersing collagen fibres of a native naturally crosslinked collagen into an acidic solution at a pH from 2 to 5 such as to produce an acidic collagen slurry,
b) mixing and homogenizing the acidic collagen slurry with particles of a biphasic CAP/HAP bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets, wherein the homogeneous coarse external surface comprises epitactically grown nanocrystalline hydroxyapatite platelets forming an interlocked network of platelets with sizes of 0.2 to 20 μm as determined by Scanning Electron Microscopy (SEM) to produce a collagen/CAP/HAP slurry, c) freeze-drying and sterilizing the collagen/CAP/HAP slurry by gamma-ray or X-ray irradiation or ethylene oxide treatment.

19. A method of promoting bone formation, bone regeneration and/or bone repair at a defect site in a subject by implanting the collagen matrix of claim 1 at the defect site, such that bone formation, bone regeneration and/or bone repair are promoted at the defect site.

20. A method of promoting osteogenic differentiation in a bone of a subject, comprising administering the collagen matrix of claim 1 to the bone of a subject, such that osteogenic differentiation is promoted in the bone of the subject.

* * * * *